(12) United States Patent
Kink et al.

(10) Patent No.: US 7,261,891 B2
(45) Date of Patent: *Aug. 28, 2007

(54) ANTIBODIES TO CYTOKINES IN THE PREVENTION AND TREATMENT OF INFLAMMATORY BOWEL DISEASE

(75) Inventors: John A. Kink, Madison, WI (US); Katherine L. Worledge, Madison, WI (US); Douglas C. Stafford, Madison, WI (US)

(73) Assignee: Promega Corporation, Madison, WI (US)

( * ) Notice: Subject to any disclaimer, the term of this patent is extended or adjusted under 35 U.S.C. 154(b) by 491 days.

This patent is subject to a terminal disclaimer.

(21) Appl. No.: 10/627,499

(22) Filed: Jul. 25, 2003

(65) Prior Publication Data

US 2005/0053604 A1 Mar. 10, 2005

Related U.S. Application Data

(63) Continuation of application No. 09/325,825, filed on Jun. 4, 1999, now Pat. No. 6,663,864, which is a continuation-in-part of application No. 09/095,535, filed on Jun. 10, 1998, now Pat. No. 6,395,273.

(51) Int. Cl.
*A61K 39/42* (2006.01)
*A61K 39/395* (2006.01)
*C07K 16/00* (2006.01)
*C12P 21/08* (2006.01)

(52) U.S. Cl. .................. 424/130.1; 424/145.1; 424/139.1; 424/158.1; 530/387.1; 530/389.1; 530/389.2

(58) Field of Classification Search .............. None
See application file for complete search history.

(56) References Cited

U.S. PATENT DOCUMENTS

| | | | |
|---|---|---|---|
| 4,477,432 A | 10/1984 | Hardie | 424/85 |
| 4,676,982 A | 6/1987 | Hassig | 424/85 |
| 4,677,064 A | 6/1987 | Mark et al. | 435/68 |
| 4,748,018 A | 5/1988 | Stolle et al. | 424/87 |
| 4,870,163 A | 9/1989 | Rubin et al. | 530/43 |
| 5,080,895 A | 1/1992 | Tokoro | 424/85.8 |
| 5,334,380 A | 8/1994 | Kilbourn et al. | |
| 5,385,901 A | 1/1995 | Kaplan et al. | 514/231.5 |
| 5,420,253 A | 5/1995 | Emery et al. | 530/423 |
| 5,436,154 A | 7/1995 | Barbanti et al. | 435/240.27 |
| 5,487,984 A | 1/1996 | Allet et al. | 435/69.5 |
| 5,604,231 A | 2/1997 | Smith et al. | 514/256 |
| 5,614,540 A | 3/1997 | Christensen | 514/362 |
| 5,654,407 A | 8/1997 | Boyle et al. | 530/388.15 |
| 5,656,272 A | 8/1997 | Le et al. | 424/133.1 |
| 5,672,347 A | 9/1997 | Aggarwal et al. | 424/139.1 |
| 5,698,195 A * | 12/1997 | Le et al. | 424/133.1 |
| 5,707,622 A | 1/1998 | Fong et al. | 424/145.1 |
| 5,753,228 A | 5/1998 | Sterling et al. | 424/151.1 |
| 5,772,999 A | 6/1998 | Greenblatt et al. | 424/187.1 |
| 5,795,967 A * | 8/1998 | Aggarwal et al. | 530/388.23 |
| 6,395,273 B1 * | 5/2002 | Kink et al. | 424/145.1 |
| 6,663,864 B1 * | 12/2003 | Kink et al. | 424/158.1 |

FOREIGN PATENT DOCUMENTS

| | | | |
|---|---|---|---|
| EP | 0 155 549 B1 | | 3/1991 |
| WO | WO92/07585 | * | 5/1992 |
| WO | WO96/33204 | | 10/1996 |
| WO | WO97/15327 | | 5/1997 |
| WO | WO98/14209 | | 4/1998 |

OTHER PUBLICATIONS

Eigler et al., Immunol. Today, Oct. 1997, vol. 18(10), pp. 487-492.*
Woolley and Landon, J. Immunol. Methods, 1995, vol. 178, pp. 253-265.*
Otto et al., Clin. Diagn. Lab. Immunol., Jul. 1997, vol. 4(4), pp. 487-490.*
Polson et al., Immunol. Commun., 1980, 9(5): 475-493. (Abstract).*
Hawkey C. J., in Inflammatory Bowel Diseases, R. N. Allan (eds), New York, Churchill Livingstone, 1997, pp. 521-534.*
Worledge et al., 2000, Dig. Dis. and Sci., 45(12):2298-2305.*
Polson et al., "Antibodies to Proteins from Yolk of Immunized Hens,"*Immunol. Comm.*, 9:495-514 (1980).
Okayasu et al.,"A Novel Method in the Induction of Reliable Experimental Acute and Chronic Ulcerative Colitis in Mice," *Gastroenterology*, 98:694-702 (1990).
Kojouharoff et al.,"Neutralization of tumour necrosis facto (TNF) but not of IL-1 reduces inflammation in chronic dextran sulphate sodium-induced colitis in mice," *Clin. Exp.Immunology*, 107:353-358 (1997).
Olson et al., "Antiserum to Tumor Necrosis Factor and failure to Prevent Murine Colitis," *J. Pediatric Gatroenterology and Nutrition* 21: 410-418 (1995).
Stack et al. , "The Effects of CDP571, An Engineered Human IgG∝4 Anti-TNF∝ Antibody in Crohn's Disease",*Gastroenterology*, 110:A1018 (1996).
Rutgeerts et al.,"Retreatment with Anti-TNF-∝ Chimeric Antibody (cA2) Effectively maintains cA3-Induced remission in Crohn's Disease," *Gastroenterology* 112:A1078 (1997).
Van Dullemen et al.,"Treatment of Crohn's Disease with Anti-Tumor Necrosis Factor Chimeric Monoclonal Antibody (cA2)," *Gastroenterology* 109:129-138 (1995).

(Continued)

*Primary Examiner*—Eileen B. O'Hara
*Assistant Examiner*—Xiaozhen Xie
(74) *Attorney, Agent, or Firm*—Medlen & Carroll, LLP

(57) ABSTRACT

Methods are described for treating inflammatory bowel disease in animals, including humans. Specific avian polyclonal antibodies directed to proinflammatory cytokines (such as IL-6 and TNF) are shown to have a beneficial effect in animal models predictive of human therapy for the treatment of colitis, including Crohn's disease.

7 Claims, 24 Drawing Sheets

OTHER PUBLICATIONS

Targan et al., "A Short-Term Study of Chimeric Monoclonal Antibody cA2 to Tumor Necrosis Factor ∝ for Crohn's Disease," *New England Journal of Medicine*, 337:1029-1035 (1997).

Plevy et al., "A Role for TNF-∝ and Mucosal T Helper-I Cytokines in the Pathogenesis of Crohn's Disease," *Journal of Immunology*, 6277-6282 (1997).

Sartor, "Current Concepts of the Etiology and Pathogenesis of Ulcerative Colitis and Crohn's Disease," *Inflammatory Bowel Disease*, 24:475-507 (1995).

Sartor, "Pathogenesis and Immune Mechanisms of Chronic Inflammatory Bowl Diseases," *Gastroenterology*, 92:5S-11S (1997).

Robinson, "Optimizing Therapy for Inflammatory Bowel Disease," *American Journal of Gastroenterology*, 92:12-17 (1997).

Targan and Shanahan, "Pseudomembranous Colitis and Clostridium Difficle Infection," Inflammatory Bowel Disease from Bench to Bench, 51:743-755 (1994).

Ogorek and Fisher, "Differentiation Between Chrohn's Disease and Ulcerative Colitis," in *Inflammatory Bowel Disease*, Katz, ed., 78:1249-1257 (1994).

Cameron, "Anti-TNF-∝ treatments set to mop up in rheumatoid arthritis," *Research and Development*, pp. 9-10 (1998).

Elliott et al., "Randomised double-blind comparison of chimeric monoclonal antibody to tomour necrosis facto ∝ (cA2) versus placebo in rheumatoid arthritis," *Lancet*, 344:1105-1110 (1994).

Elliott et al., "Repeated therapy with monoclonal antibody to tomour necrosis factor ∝ (cA2) in patients with rheumatoid arthritis," *Lancet* 344:1125-1127 (1994).

Gibson, "Inflammatory Bowel Disease Current Concepts in Pathogenesis and Therapy," *Clin. Immunother.*, 2(2):135-160 (1994).

Bell and Wallace, "Inflammatory Bowel Disorders Current and Future Drugs that Modulate Adhesion Molecules," *Biodrugs*, 7(4):273-284 (1997).

Opal et al., "Potential Hazards of Combination Immunotherapy in the Treatment of Experimental Septic Shock," *J. Infect. Dis.*, 173:1415-1421(1996).

Russell et al., "Combined Inhibition of Interleukin-1 and Tumor Necrosis Factor in Rodent Endotoxemia: Improved Survival and Organ Function," *J. Infect. Dis.* 171:1528-1538(1995).

Levine et al., "Intravenous Immunoglobulin Therapy for Active, Extensive and Medically Refractory Idiopathic Ulcerative or Crohn's Colitis" *Am J Gastroenterol*, 87:91-100 (1992).

Neurath et al., "Predominant Pathogenic role of Tumor Necrosis Factor in Experimental Colitis in Mice," *Eur J Immunol* 27:1743-1750 (1997).

Neurath et al., "Antibodies to Interleukin 12 Abrogate Established Experimental Colitis in mice," *J Exp Med* 182:1281-1290 (1995).

Feldmann et al., "Cytokine Expression and Networks in Rheumatoid Arthritis: Rationale for Anti-TNFanpha Antibody Therapy and its Mechanism of Action," *J Inflammation* 47:90-96 (1996).

Reimund et al., "Increased production of tumor necrosis factor-alpha, interleukin-I-beta and interleukin-6 by morphologically normal interstinal biopsies from patients with Crohn's disease" *Gut* 39:684-689 (1996).

Duchmann et al., "Tolerance towewards resistant intestinal flora in mice is abrogated in experimental colitis and restored by treatment with interleukin-10 or antibodies to interleukin-12," *Eur J Immunol* 26:934-938 (1996).

Tsubokura et al., "Oral administration of antibodies as prophylaxis and therapy in *Campylobacter jejuni*-infected chickens," *Clin Exp Immunol* 108:451-455 (1997).

Nicholls et al., "Cytokines in stools of children with inflammatory bowel disease or infective diarrrhoea," *J Clin Path* 46:757-760 (1993).

Tjellström et al., "Oral immunoglobulin treatment in Crohn's disease," *Acta Paediatr* 86:221-223 (1997).

Rubalteli et al., "Prevention of necrotizing enterocolitis in neonates at risk by oral administration of monomeric IgG," *Dev Pharmacol Ther* 17:138-143 (1991).

Armstrong et al., "Tumor necrosis factor and inflammatory bowel disease," *British Journal of Surgery* 84:1051-1058 (1997).

Monteleone et al., "Interleukin 12 (IL-12) is expressed and actively released by Crohn's disease intestinal lamina propria mononuclear cells (LPMCs)," *Gastroenterology* 112:1169-1178 (1997).

Starnes et al., "Anti-IL-6 monoclonal antibodies protect against lethal *Escherichia coli* infection and lethal tumor necrosis factor-alpha challenge in mice" *J Immuno* 12:4185-4191 (1990).

Doherty et al., "Evidence for IFN-gama as a mediator of the lethality of endotoxin and tumor necrosis factor-alpha" *J Immuno* 5:1666-1670 (1992).

Manthey et al., "The role of cytokines in host responses to endotoxin" *Reviews in Med Microbio* 3:72-79 (1992).

Dalekos, et al., "High concentrations of soluable interleukin-2 receptors and interleukin-6 in active ulcerative cells" *Hellenic J Gastro* 8:319-327 (1995).

Evans, et al., "Treatment of ulcerative colitis with an engineered human anti-TNF-alpha antibody CDP571" *Aliment Pharmacol Ther* 11:1031-1035 (1997).

Hoang, et al., "Symposium: Role of cytokines in inflammatory bowel disease" *Acte Gastro-Enterologica Belgica* 57:219-223 (1994).

van Hogezand, et al., "Selective immunomodulation in patients with inflammatory bowel disease-future therapy or reality?" *Netherlands J of Med* 48:64-67 (1996).

Zacharchuk et al., "Macrophage-mediated cytotoxicity: Role of a soluble macrophage cytotoxic factor similar to hymphotoxin and tumor necrosis factor," *PNAS USA* 80:6341-6345 (1983).

Zacharchuk, Charles Michael, "A Macrophage Cytotoxic Factor: Immunochemical and Functional Characterization," Dissertation Abstract (1983).

Pennica et al., "Human tumor necrosis factor: precursor structure, expression and homology to lymphotoxin," *Nature* 312:724-729 (1984).

Ruff, Michael Roland, "Mechanism of Action of a Serum Oncolytic Protein, Rabbit Tumor Necrosis Factor," Dissertation Abstract. (1980).

Beck et al., "Cytokines in inflammatory bowel disease," *Mediators of Inflammation* 6:95-103 (1997)

\* cited by examiner

ANTIBODIES TO CYTOKINES IN THE PREVENTION AND TREATMENT OF INFLAMMATORY BOWEL DISEASE

The present application is a Continuation of U.S. application Ser. No. 09/325,825 filed on Jun. 4, 1999, now U.S. Pat. No. 6,663,864 which in turn is a continuation-in-part of U.S. patent application Ser. No. 09/095,535, filed Jun. 10, 1998, now U.S. Pat. No. 6,395,273.

FIELD OF THE INVENTION

The present invention relates to therapeutics for the prevention and treatment of inflammatory bowel disease, and in particular the prevention and treatment of inflammatory bowel disease in humans as well as other animals through the use of antibodies to inflammatory mediators including but not limited to proinflammatory cytokines.

BACKGROUND OF THE INVENTION

Inflammatory bowel diseases (IBD) are defined by chronic, relapsing intestinal inflammation of obscure origin. IBD refers to two distinct disorders, Crohn's disease and ulcerative colitis (UC). Both diseases appear to result from the unrestrained activation of an inflammatory response in the intestine. This inflammatory cascade is thought to be perpetuated through the actions of proinflammatory cytokines and selective activation of lymphocyte subsets. In patients with IBD, ulcers and inflammation of the inner lining of the intestines lead to symptoms of abdominal pain, diarrhea, and rectal bleeding. Ulcerative colitis occurs in the large intestine, while in Crohn's, the disease can involve the entire GI tract as well as the small and large intestines. For most patients, IBD is a chronic condition with symptoms lasting for months to years. It is most common in young adults, but can occur at any age. It is found worldwide, but is most common in industrialized countries such as the United States, England, and northern Europe. It is especially common in people of Jewish descent and has racial differences in incidence as well. The clinical symptoms of IBD are intermittent rectal bleeding, crampy abdominal pain, weight loss and diarrhea. Diagnosis of IBD is based on the clinical symptoms, the use of a barium enema, but direct visualization (sigmoidoscopy or colonoscopy) is the most accurate test. Protracted IBD is a risk factor for colon cancer, and treatment of IBD can involve medications and surgery.

Some patients with UC only have disease in the rectum (proctitis). Others with UC have disease limited the rectum and the adjacent left colon (proctosigmoiditis). Yet others have UC of the entire colon (universal IBD). Symptoms of UC are generally more severe with more extensive disease (larger portion of the colon involved with disease).

The prognosis for patients with disease limited to the rectum (proctitis) or UC limited to the end of the left colon (proctosigmoiditis) is better then that of full colon UC. Brief periodic treatments using oral medications or enemas may be sufficient. In those with more extensive disease, blood loss from the inflamed intestines can lead to anemia, and may require treatment with iron supplements or even blood transfusions. Rarely, the colon can acutely dilate to a large size when the inflammation becomes very severe. This condition is called toxic megacolon. Patients with toxic megacolon are extremely ill with fever, abdominal pain and distention, dehydration, and malnutrition. Unless the patient improves rapidly with medication, surgery is usually necessary to prevent colon rupture.

Crohn's disease can occur in all regions of the gastrointestinal tract. With this disease intestinal obstruction due to inflammation and fibrosis occurs in a large number of patients. Granulomas and fistula formation are frequent complications of Crohn's disease. Disease progression consequences include intravenous feeding, surgery and colostomy.

Colon cancer is a known complication of chronic IBD. It is increasingly common in those patients who have had extensive IBD over many years. The risk for cancer begins to rise significantly after eight to ten years of IBD.

IBD may be treated medicinally. The most commonly used medications to treat IBD are anti-inflammatory drugs such as the salicylates. The salicylate preparations have been effective in treating mild to moderate disease. They can also decrease the frequency of disease flares when the medications are taken on a prolonged basis. Examples of salicylates include sulfasalazine, olsalazine, and mesalamine. All of these medications are given orally in high doses for maximal therapeutic benefit. These medicines are not without side effects. Azulfidine can cause upset stomach when taken in high doses, and rare cases of mild kidney inflammation have been reported with some salicylate preparations.

Corticosteroids are more potent and faster-acting than salicylates in the treatment of IBD, but potentially serious side effects limit the use of corticosteroids to patients with more severe disease. Side effects of corticosteroids usually occur with long term use. They include thinning of the bone and skin, infections, diabetes, muscle wasting, rounding of faces, psychiatric disturbances, and, on rare occasions, destruction of hip joints.

In IBD patients that do not respond to salicylates or corticosteroids, medications that suppress the immune system are used. Examples of immunosuppressants include azathioprine and 6-mercaptopurine. Immunosuppressants used in this situation help to control IBD and allow gradual reduction or elimination of corticosteroids. However, immunosuppressants render the patient immuno-compromised and susceptible to many other diseases.

Clearly there is a great need for agents capable of preventing and treating IBD. It would be desirable if such agents could be administered in a cost-effective and timely fashion, with a minimum of adverse side effects.

DEFINITIONS

The present invention contemplates the treatment and prevention of IBD through the use of antibodies to inflammatory mediators, and in particular, antibodies to proinflammatory cytokines. The term "inflammatory mediator" refers to a variety of classes of molecules involved in an inflammatory response, including but not limited to proinflammatory phospholipids, chemokines [having both the C-C (e.g., Rantes, MIP-1α) and CXC (e.g., GRO-α, IP-10, etc.) motifs), adherence proteins (e.g., ICAM-1, selectin, VCAM, etc), leukotrienes, and cytokines (e.g., interleukins).

The phrase "symptoms of IBD" is herein defined to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding). The phrase "wherein said symptoms are reduced" refers to a qualitative or quantitative reduction in detectable symptoms, including but not limited to a detectable impact on the rate of recovery from disease (e.g. rate of weight gain).

The phrase "at risk for IBD" is herein defined as encompassing the segment of the world population that has an increased risk for IBD. IBD is most commonly found in young adults, but can occur at any age. It occurs worldwide, but is most common in the United States, England, and northern Europe. It is especially common in people of Jewish descent. An increased frequency of this condition has been recently observed in developing nations.

The present invention contemplates administration to or at the lumen. The phrase "administered to or at the lumen" or the like is herein defined as delivery to the space in the interior of the intestines. Such delivery can be achieved by a variety of routes (e.g., oral, rectal, etc.) in a variety of vehicles (e.g., tablet, suppository, etc.). In one embodiment, administration to or at the lumen results in delivery of antibody to the lamina propria (or regions of the intenstinal wall or radial to the mucosa). The lamina propria is classified as a loose, areolar, connective tissue but with lymphatic tendencies, the lymphoid material presumably functioning as a defense barrier against bacterial infection. When the antibody of the present invention is administered, the presence of the antibody in the intestinal wall can be readily detected by conventional means (e.g., staining and histology, labeled antibody and imaging, etc.).

SUMMARY OF THE INVENTION

The present invention relates to therapeutics for the prevention and treatment of IBD. Specifically, the present invention contemplates the prevention and treatment of IBD in humans as well as other animals through the use of antibody therapy.

It is not intended that the present invention be limited to a particular type of antibody. Polyclonal and monoclonal antibodies are contemplated in the context of the present invention. Such antibodies may be made in a variety of animals [e.g., rabbits, horses, cows (e.g., in the milk), and birds]. The present invention also contemplates human and "humanized" antibodies.

It is preferred that the antibodies not be complement fixing. More specifically, avian antibodies (e.g., chicken antibodies from eggs) are preferred. It is contemplated that the treatment with such antibodies will have the desired result of reducing the symptoms (as well as morbidity and mortality) caused by IBD.

In one embodiment, the present invention contemplates a method comprising the administration of antibodies which bind to inflammatory mediators such as TNF. Preferably, the antibody is reactive with TNF across species. Specifically, the present invention demonstrates that immunization with human TNF generates neutralizing antibody capable of reacting with endogenous murine TNF. Thus, the present invention provides anti-TNF antibody that will react with mammalian TNF generally.

It is not intended that the present invention be limited to antibodies to TNFα. As demonstrated herein, antibodies to mediators believed to be downstream in the inflammatory cascade from TNF, such as IL-6 or IL-12 are effective. Such antibodies can be used preventively or (as demonstrated in an experimental model of IBD) during the acute stage of pathogenesis. While some previous work described in the literature has suggested that the use of TNF antibodies in the acute phase of IBD is contraindicated, the data contained herein indicates otherwise.

In another embodiment, the antibodies are combined with other reagents including but not limited to other antibodies. In one such embodiment, therapy comprises administration of a formulation comprising antibodies to a first cytokine and a second cytokine (e.g. antibodies to both TNF and IL-6).

In another embodiment, the present invention contemplates a method of relieving symptoms of and rescuing mammals (including humans) from episodes of acute or chronic IBD utilizing anti-cytokine antibodies such as anti-TNF antibodies.

In another embodiment, the present invention contemplates a method of relieving symptoms of and rescuing mammals (including humans) from episodes of acute or chronic IBD utilizing a combination comprising anti-TNF antibodies. The present invention contemplates a method of treatment, comprising: (a) providing i) a mammal for treatment; ii) a therapeutic preparation, comprising anti-TNF polyclonal antibodies and (b) administering said antibodies to the lumen of said mammal.

In another embodiment, the present invention also contemplates a method of treatment, comprising: a) providing: i) a human patient with symptoms of inflammatory bowel disease, ii) a therapeutic formulation comprising avian polyclonal antibodies directed to TNF, and; b) administering said formulation to said patient.

In another embodiment, the present invention also contemplates a method of treatment, comprising: a) providing: i) a human patient with symptoms of inflammatory bowel disease, ii) a therapeutic formulation comprising avian polyclonal antibodies directed to IL-6, and; b) administering said formulation to said patient.

In another embodiment, the present invention also contemplates a method of treatment, comprising: a) providing: i) a human patient with symptoms of inflammatory bowel disease, ii) a therapeutic formulation comprising avian polyclonal antibodies directed to IL-6 and TNF, and; b) administering said formulation to said patient.

In another embodiment, the present invention also contemplates a method of treatment, comprising: a) providing: i) a human patient with symptoms of Crohn's disease, ii) a therapeutic formulation comprising avian polyclonal antibodies directed to TNF, and; b) administering said formulation to said patient.

In another embodiment, the present invention also contemplates a method of treatment, comprising: a) providing: i) a human patient with symptoms of Crohn's disease, ii) a therapeutic formulation comprising avian polyclonal antibodies directed to IL-6, and; b) administering said formulation to said patient.

In another embodiment, the present invention also contemplates a method of treatment, comprising: a) providing: i) a human patient with symptoms of Crohn's disease, ii) a therapeutic formulation comprising avian polyclonal antibodies directed to IL-6 and TNF, and; b) administering said formulation to said patient.

In the above embodiments, it is preferred that said administering is done under conditions such that said symptoms of IBD (e.g. symptoms of Crohn's disease) are reduced.

It is not intended that the present invention be limited to specific preparations of antibodies. However, polyclonal antibodies are preferred. Most importantly, it is preferred that the antibodies not be complement fixing. More specifically, avian antibodies (e.g. chicken antibodies from eggs) are preferred.

The treatment with the antibodies has the unexpected result of reducing mortality rates in animals when administered after the onset of a chronic or acute IBD episode.

DESCRIPTION OF THE DRAWINGS

FIG. 2A shows the highest oral dose of anti-TNF prevented TNBS-induced animal weight loss as compared to the vehicle control and lower doses (*n=8, p, 0.05 for all time points). The 7.5 mg/Day dose at days 6 and 10, and on day 7 was higher than the vehicle group (*n=8, p, 0.05) FIG. 2B shows oral treatment with anti-TNF reduced the mean total colon weight at all doses measured The 120 mg/day dose is statistically significant as compared to the vehicle and lower doses (*n=8, $p<0.005$, $p<0.01$) FIG. 2C shows oral treatment with the highest dose of anti-TNF significantly reduced the histological damage as compared to the vehicle and two other doses (*n=8, $p<0.0025$, $p<0.005 p<0.025$) FIG. 2D shows oral administration of 120 mg/day of anti-TNF significantly reduces MPO levels as compared to the vehicle control as well as the 75 mg/day and 30 mg/day doses.

FIG. 3A shows oral delivery of anti-TNF antibodies reduced colonic weight gain associated with TNBS treatment. The anti-TNF reduction was statistically significant compared to the preimmune treated control (*n=8, $p<0.001$) FIG. 3B shows oral delivery of anti-TNF reduced histological damage for rats treated with TNBS as compared to vehicle (n=7, *p, 0.05) and preimmune controls (N=8, *p<0.001) Normal control was zero FIG. 3C shows treatment with anti-TNF reduces histological damage as compared to the vehicle and preimmune control animals (*n=7, $p<0.05$ and $p<0.0025$ respectively) Normal control was zero. FIG. 3D shows oral delivery of anti-TNF antibodies significantly reduced the levels of tissue mysloperoxidase after rat treatment with TNBS as compared to the preimmune (*n=7, $p<0.05$)

FIG. 4A shows oral administration of anti-TNF antibodies to rats 48 hours post treatment with TNBS significantly decreased disease associated colonic weight gain as compared to vehicle treated animals (*p<0.05) saw no improvement over controls FIG. 4B shows oral administration of anti-TNF antibodies to rats 48 hours post treatment with TNBS significantly decreased morphological damage as compared to vehicle control (n=7, *p<0.005). FIG. 4C shows treatment with anti-TNF significantly reduces histological damage as compared to the sulfasalazine and vehicle treated controls (*n=7, $p<0.01$ and $p<0.001$ respectively). FIG. 4D shows oral administration of anti-TNF antibodies to rats 48 hours post TNBS treatment significantly reduced the tissue mysloperoxidase as compared to vehicle (n=7, *p<0.002) and sulfasalazine (n=7, *p<0.02).

FIG. 5A shows oral administration of anti-TNF and dexamethasone significantly reduce total colon weight as compared to the vehicle control (n=9, *p<0.025 and p<0.05 respectively). FIG. 5B shows oral administration with anti-TNF significantly reduces morphological damage as compared to the vehicle and dexamethasone treated groups (*n=9, $p<0.05$ and $p<0.025$ respectively). FIG. 5C shows oral administration with anti-TNF significantly reduces histological damage as cmopared to the dexamethasone and vehicle treated animals (*n=9, $p<0.001$ and $p<0.01$). FIG. 5D shows oral administration of anti-TNF significantly reduces mysloperoxidase levels as compared to dexamethasone treated animals (*n=9, $p<0.05$).

FIG. 6A shows oral treatment with anti-TNF significantly decreases the colon weight as compared to the vehicle and preimmune controls (*p<0.025 vs. vehicle and preimmune). FIG. 6B shows oral treatment with anti-TNF significantly decreases morphological damage as compared to the vehicle and preimmune controls (*p<0.025 vs. vehicle and preimmune). FIG. 6C shows oral treatment with anti-TNF significantly decreases the microscopic damage as compared to vehicle and preimmune controls (p<0.025 and p<0.01 respectively).

FIG. 8A shows intrarectal delivery with anti-TNF after 5 days of DSS treatment significantly reduced ocult blood found in the stool of DSS treated mice as compared to the vehicle control (*p<0.05). FIG. 8B shows intrarectal treatment with anti-TNF antibodies after 5 days of DSS treatment significantly reduced histological damage as compared to vehicle control (*p<0.02) FIG. 8C shows intrarectal delivery of anti-TNF antibodies after 5 days of DSS treatment decreased tissue myeloperoxidase levels as compared to the vehicle control (*p<0.05) and the preimmune control (*p<0.05).

DESCRIPTION OF THE INVENTION

Figure 1:
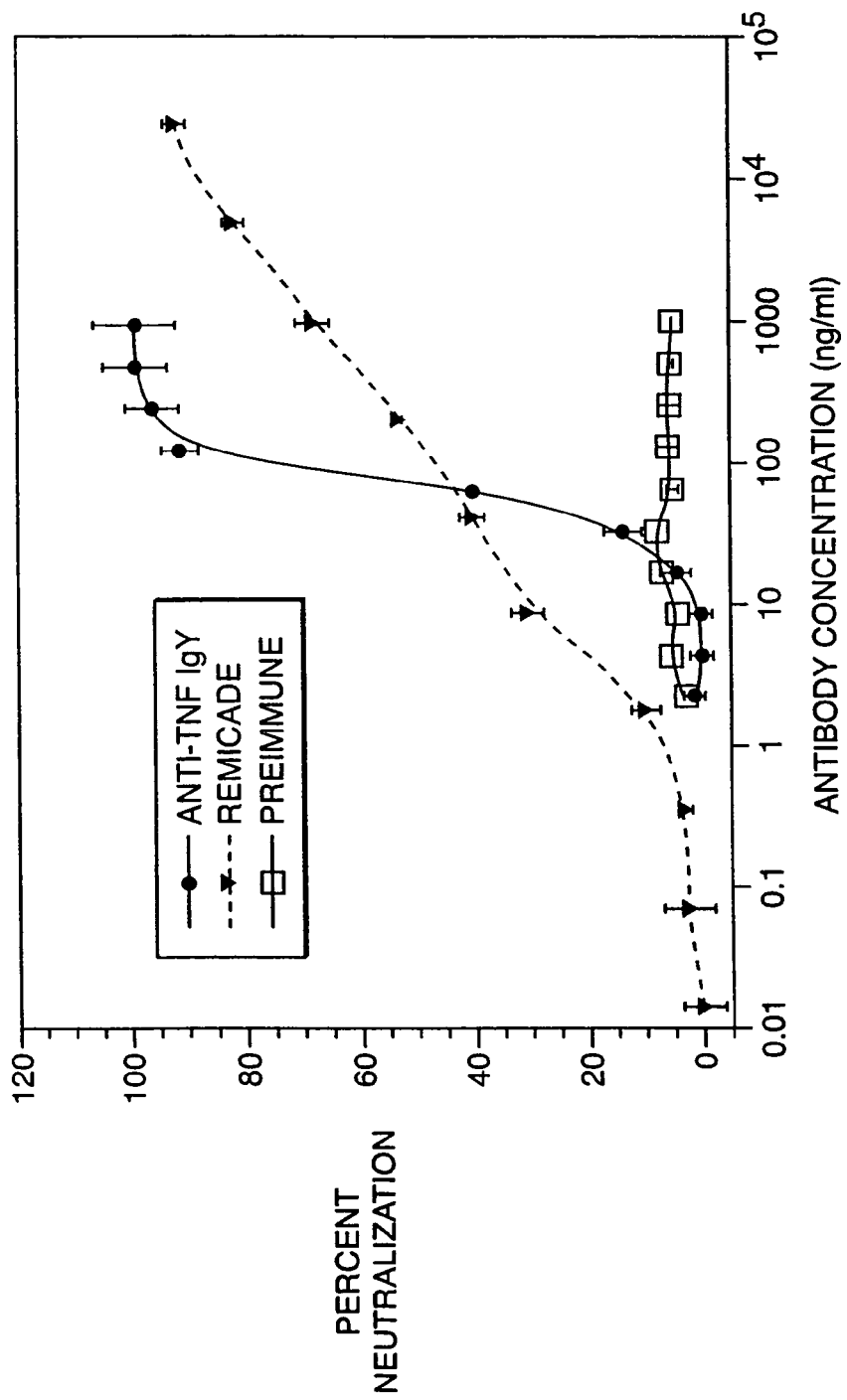
FIG. 1 is a graph showing results of the cell based TNF neutralization assay with antibodies of the present invention compared to a control antibody. The L929 cell hased assay shows the greater neutralization ability of anti-TNF IgY as compared to REMICADE. The dose of antibody which prevents 50 percent of the cytotoxicity associated with TNF (ND50) is 70 ng/ml for the anti-TNF IgY and 140 ng/ml for REMICADE. Note the concentrations graphed for the REMICADE antibody represent the total amount of specific antibody, whereas the anti-TNF IgY concentrations represent total Igy Concentrations.
Figure 2A:
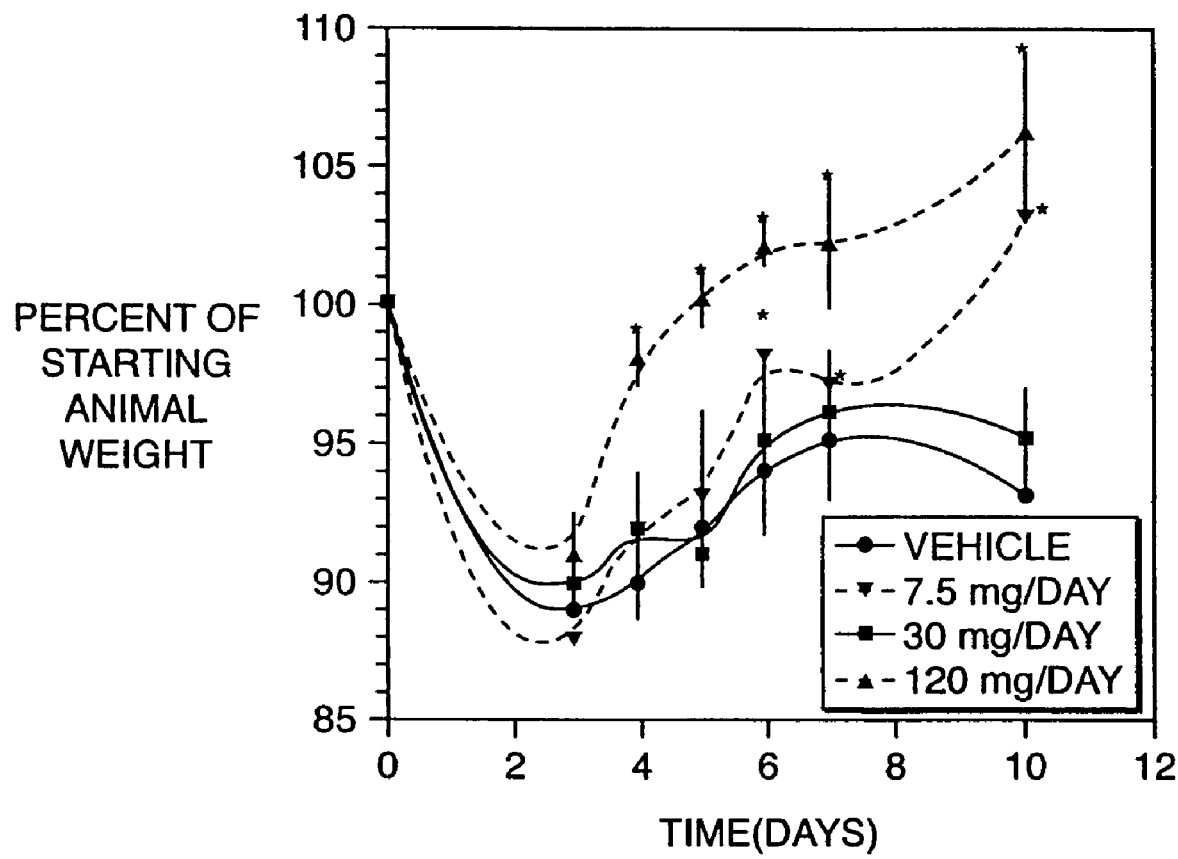
FIGS. 2A through 2D show results of a dose response study in a rat model for IBD using different concentrations of one embodiment of the anti-cytokine antibody of the present invention (i.e. anti-TNF IgY).
Figure 2B:
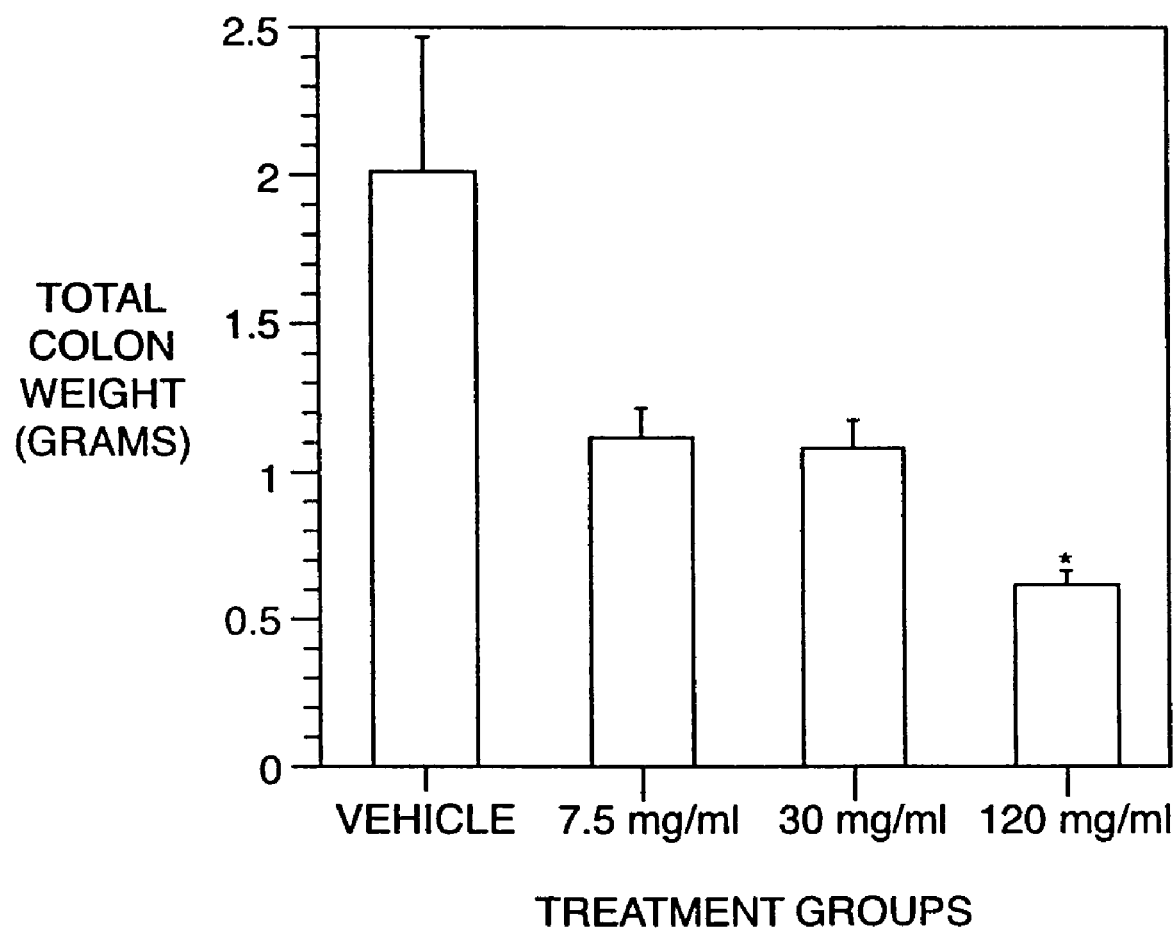
Figure 2C:
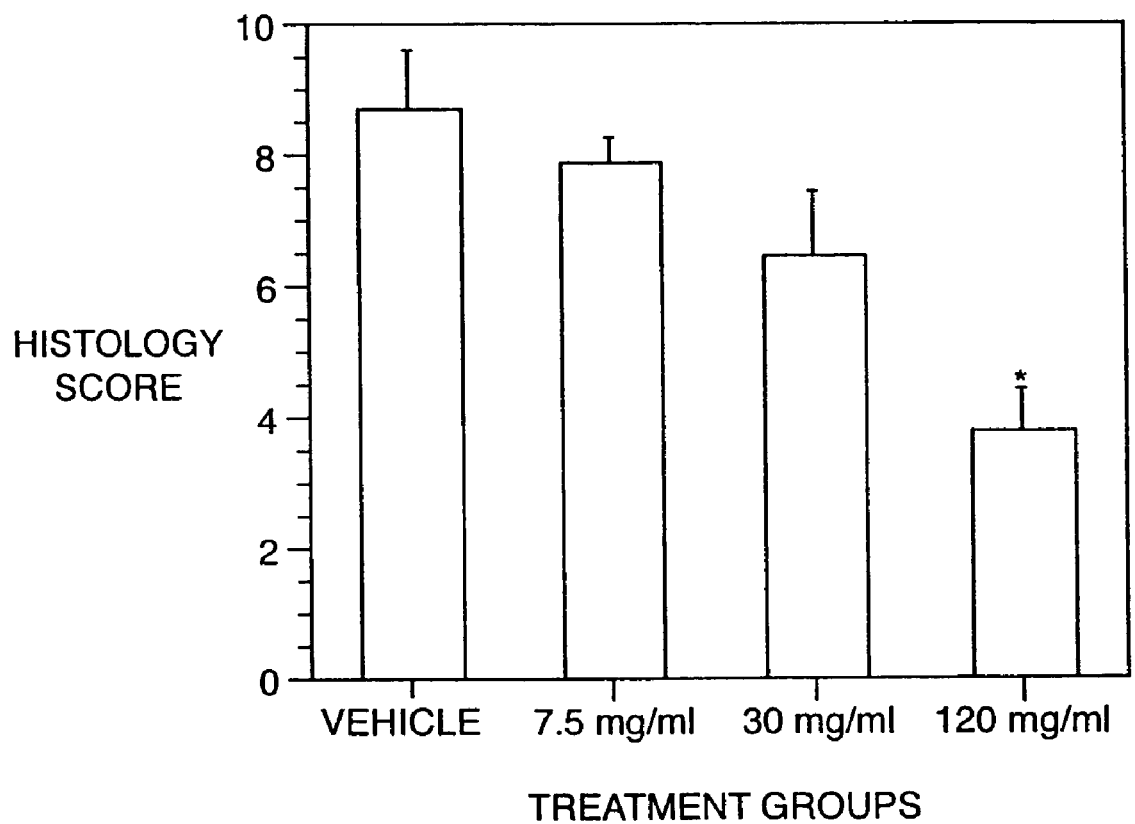
Figure 2D:
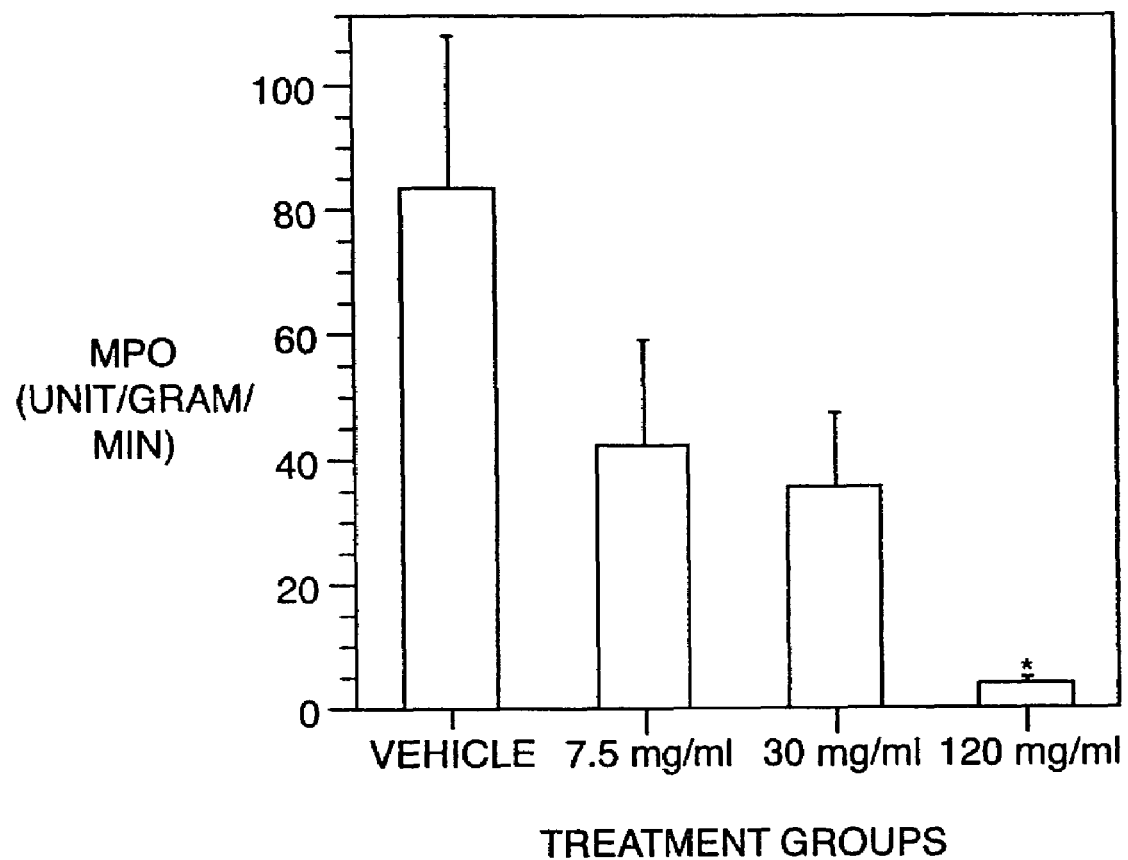
Figure 3A:
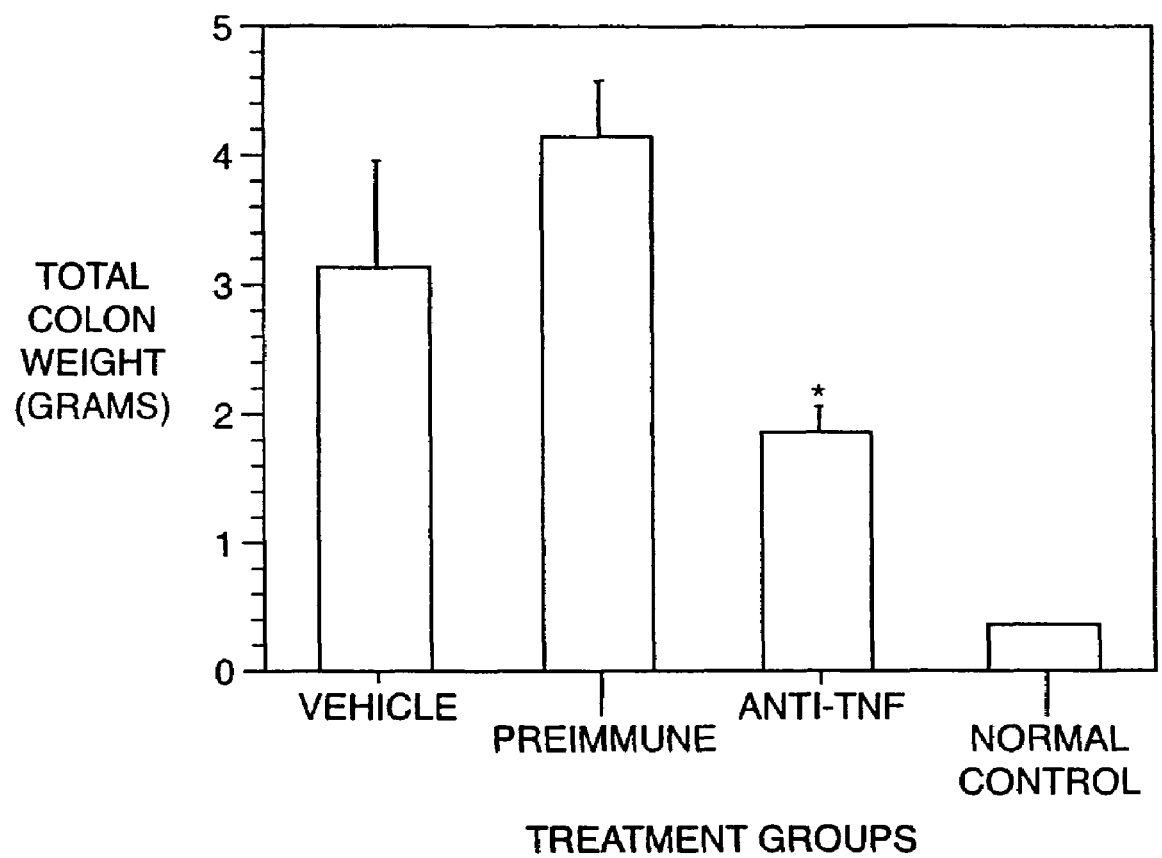
FIGS. 3A through 3D are bar graphs showing the results after pre-challenge treatment with vehicle, preimmune IgY, or an anti-TNF IgY antibody of the present invention.
Figure 3B:
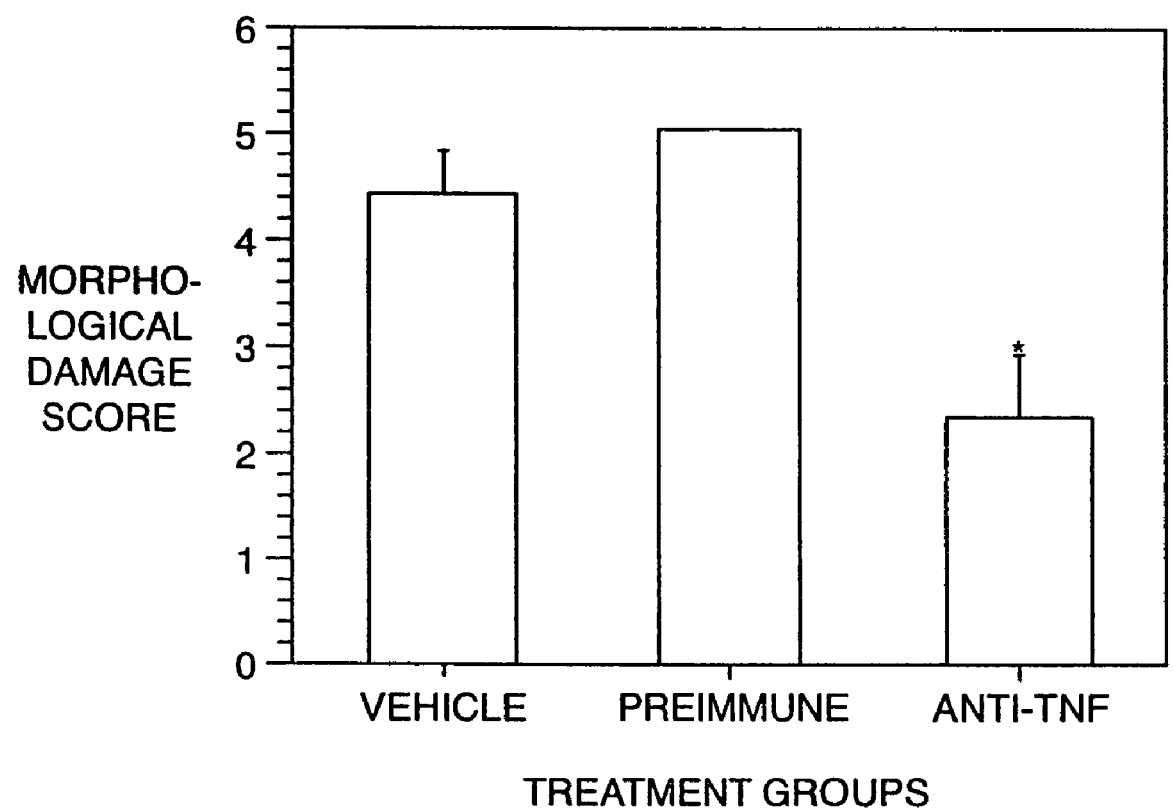
Figure 3C:
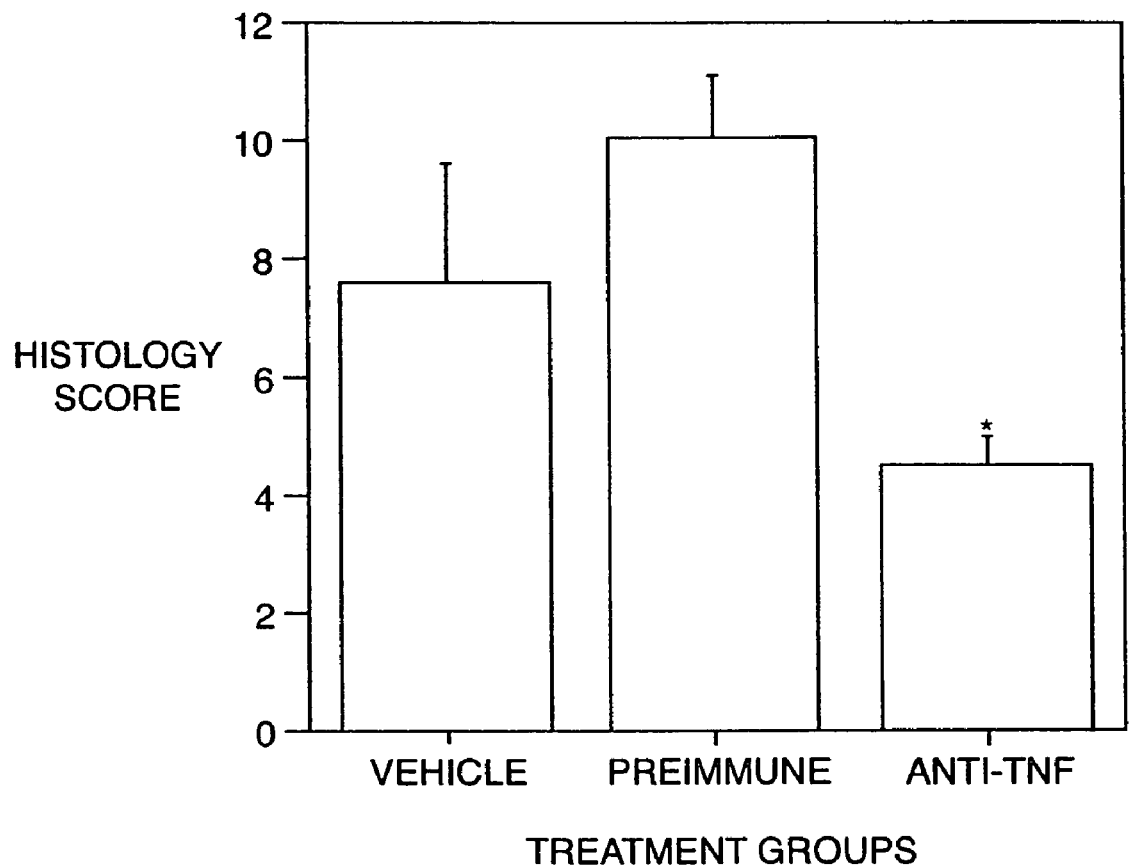
Figure 3D:
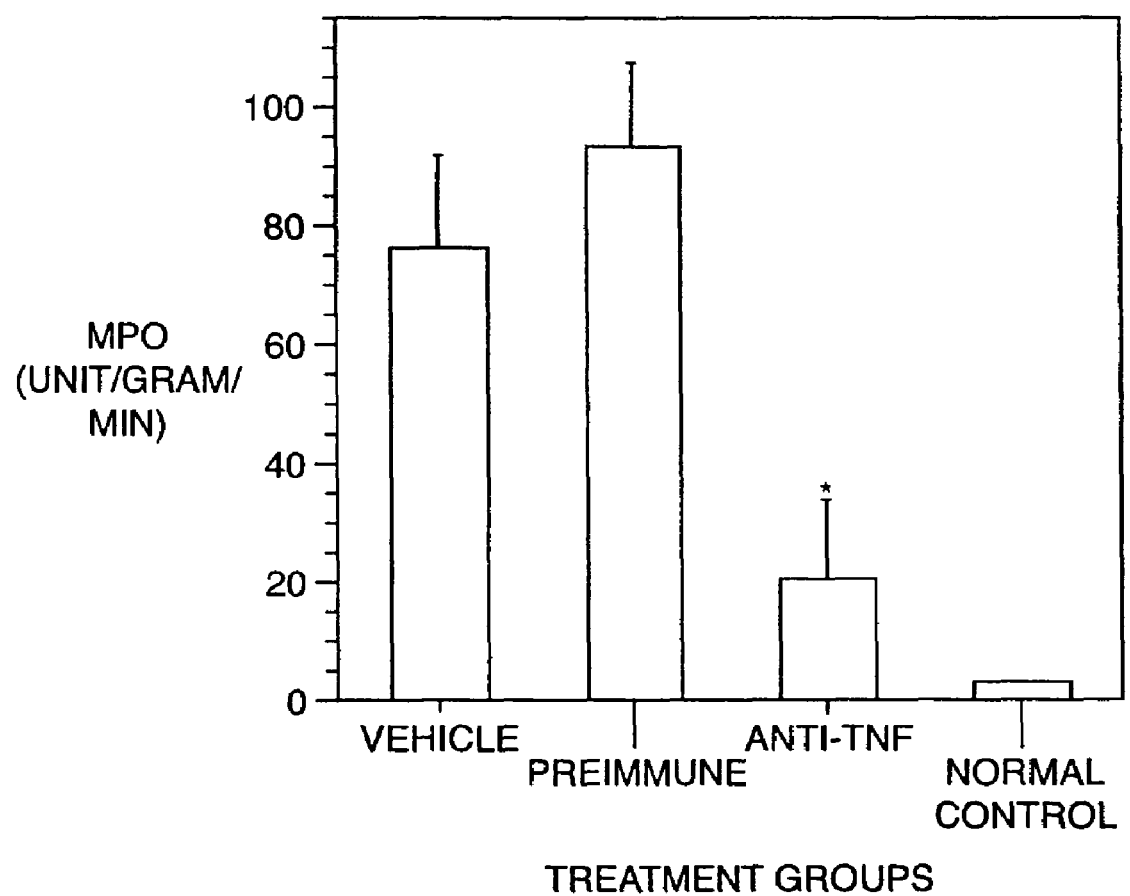
Figure 4A:
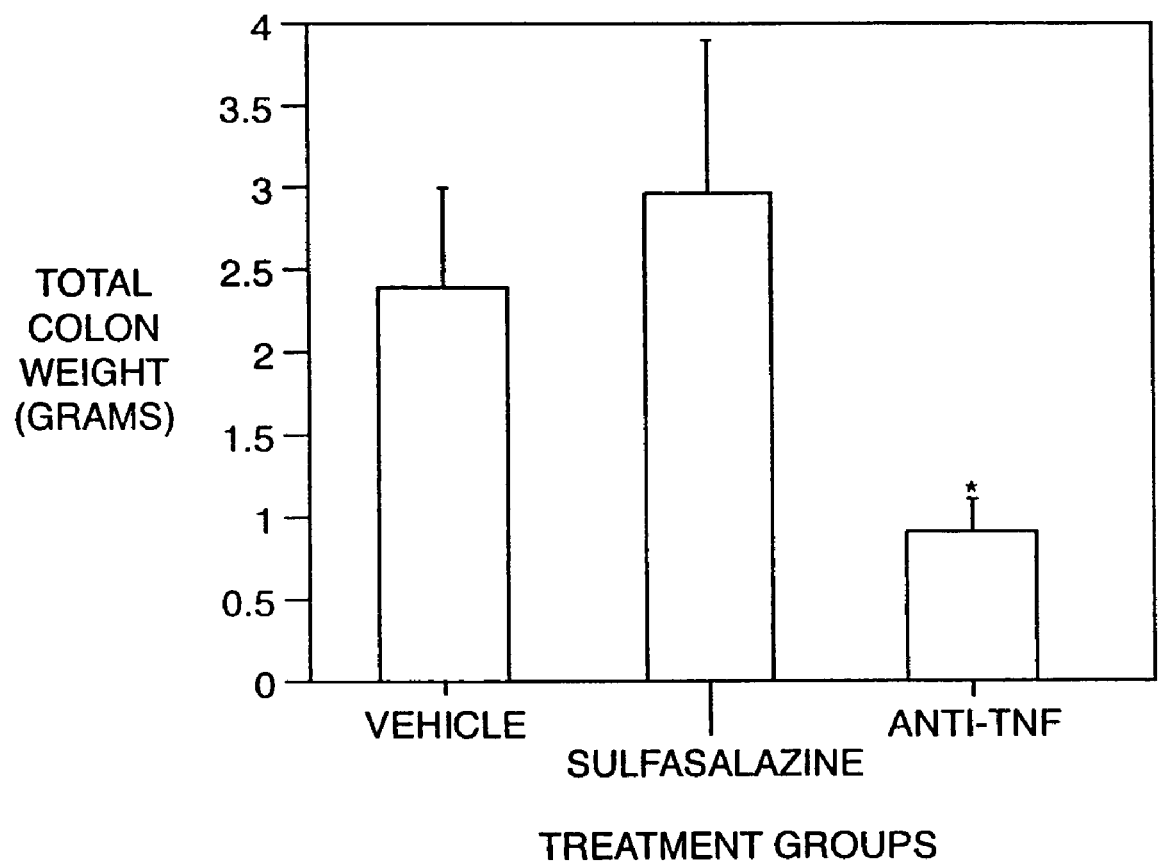
FIGS. 4A through 4D are bar graphs showing the results after post-challenge (48 hours) treatment with vehicle, sulfasalazine, or an anti-TNF IgY antibody of the present invention.
Figure 4B:
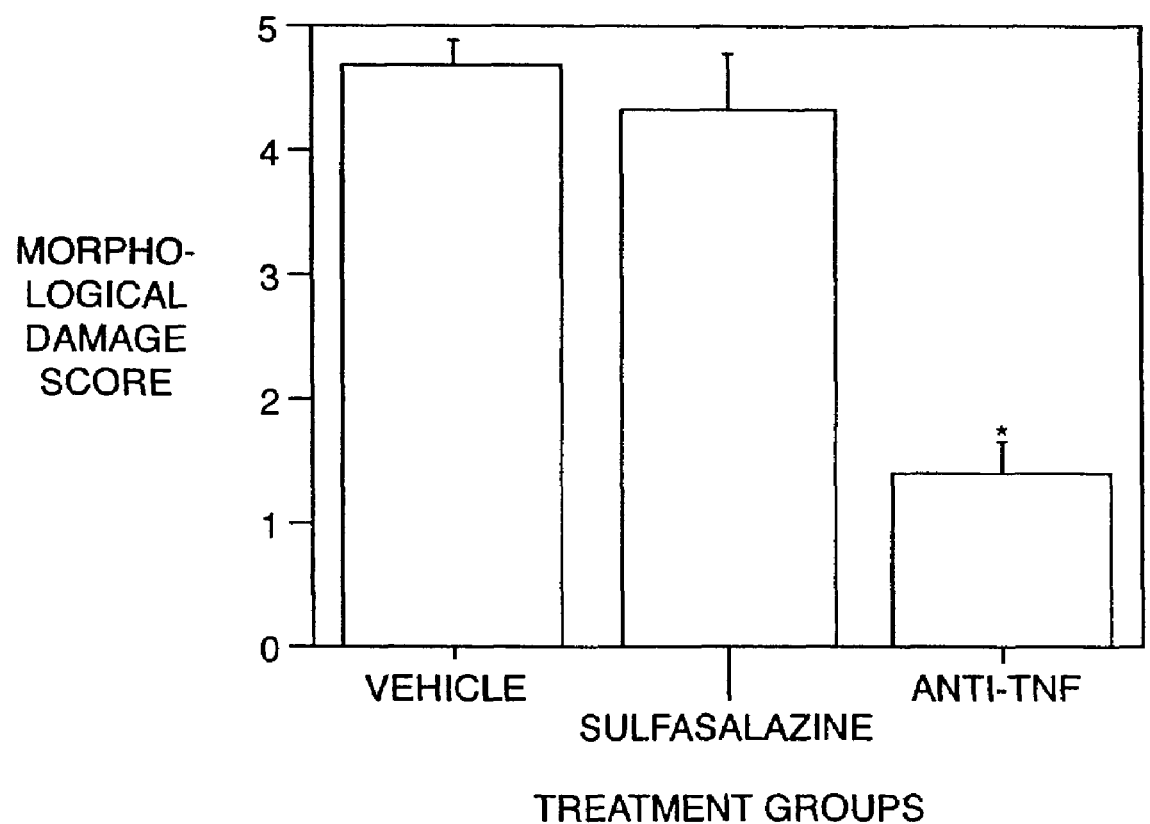
Figure 4C:
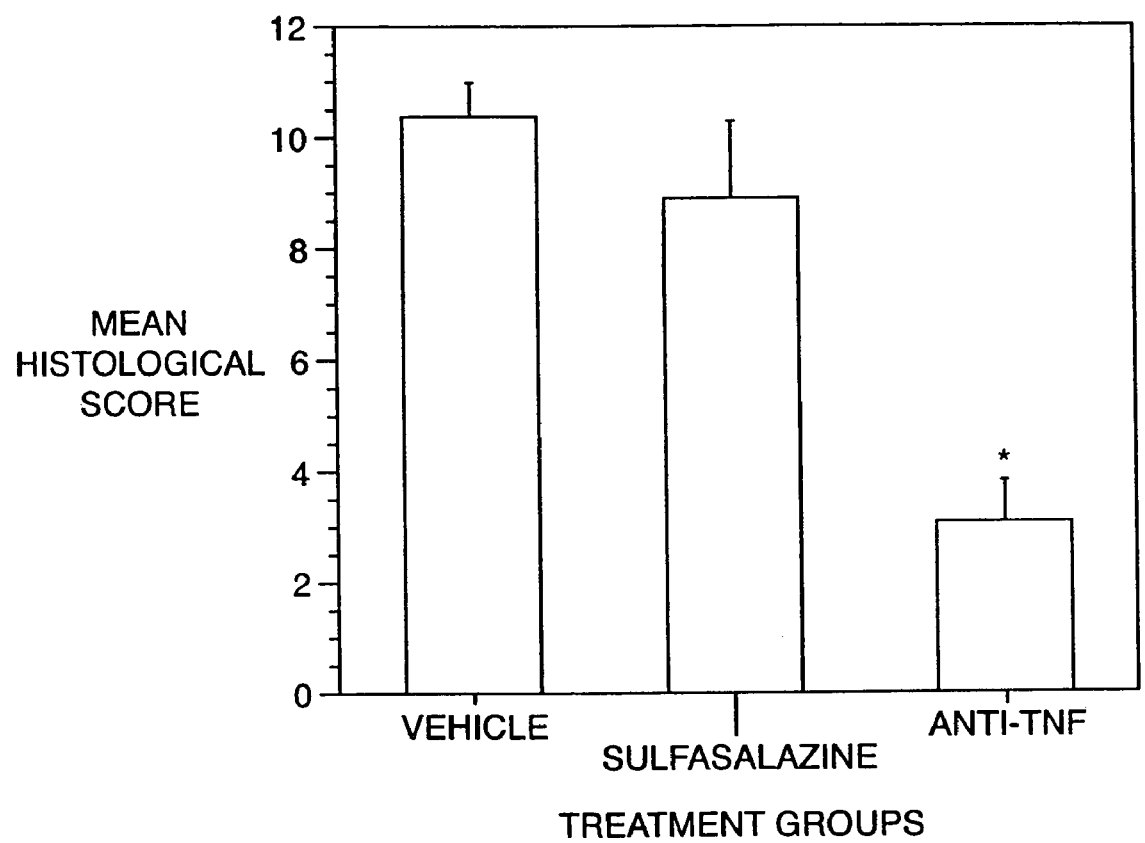
Figure 4D:
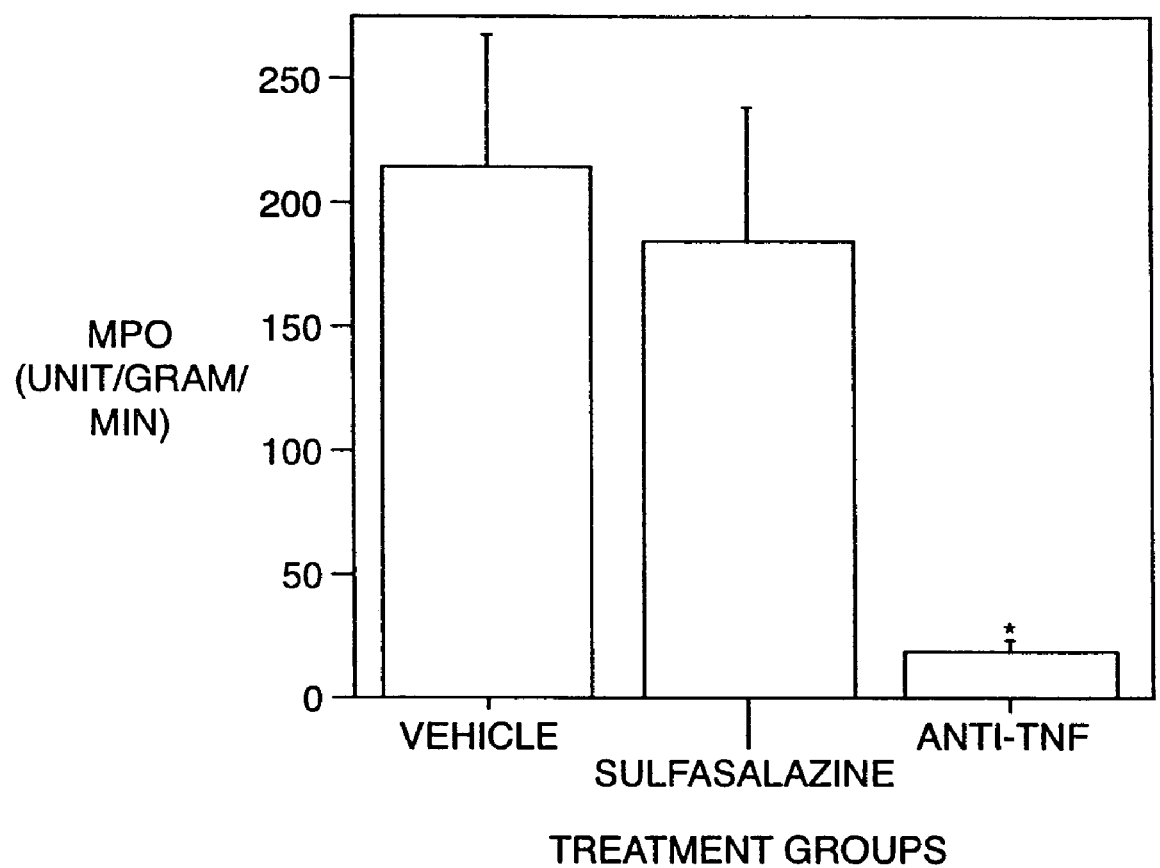
Figure 5A:
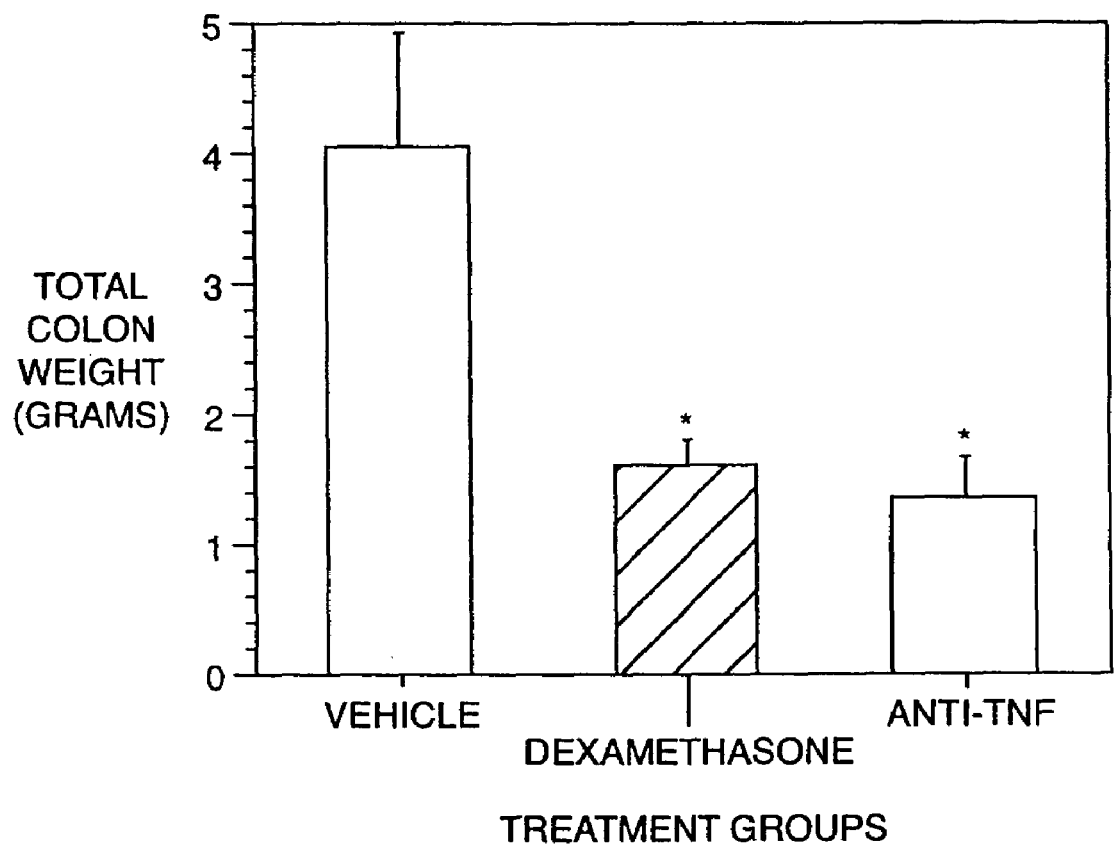
FIGS. 5A through 5D are bar graphs showing the results after pre-challenge treatment with vehicle, dexamethasone, or an anti-TNF IgY antibody of the present invention.
Figure 5B:
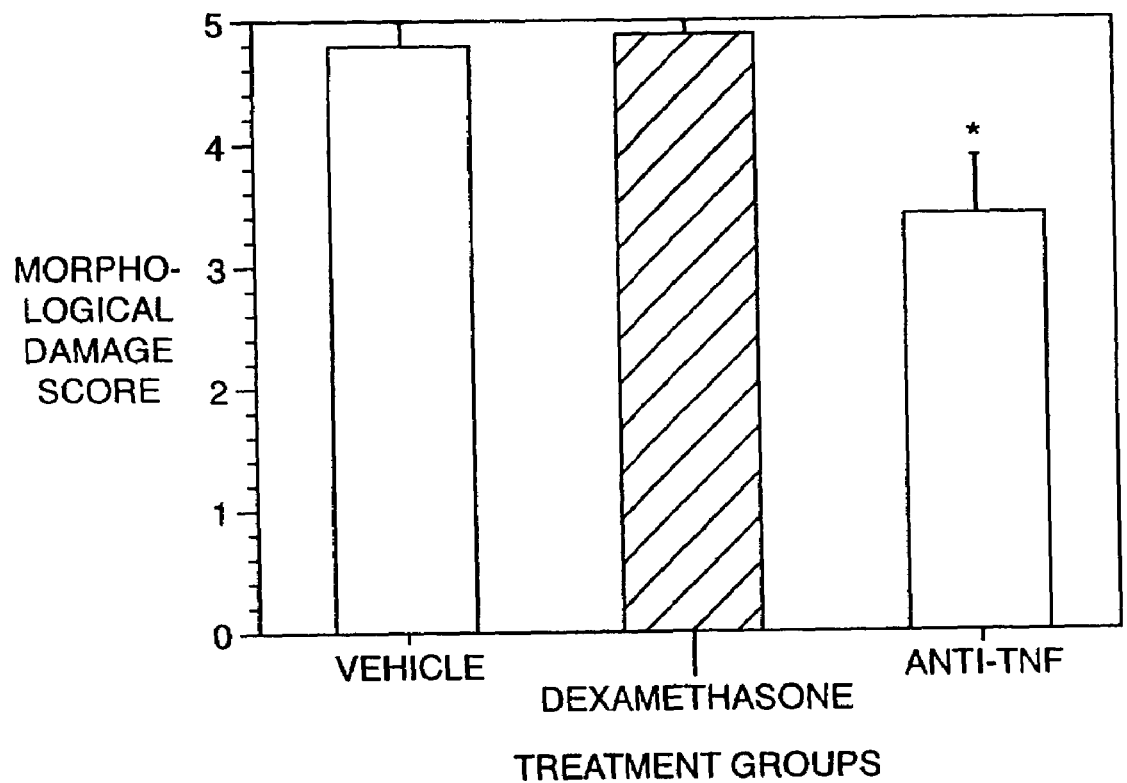
Figure 5C:
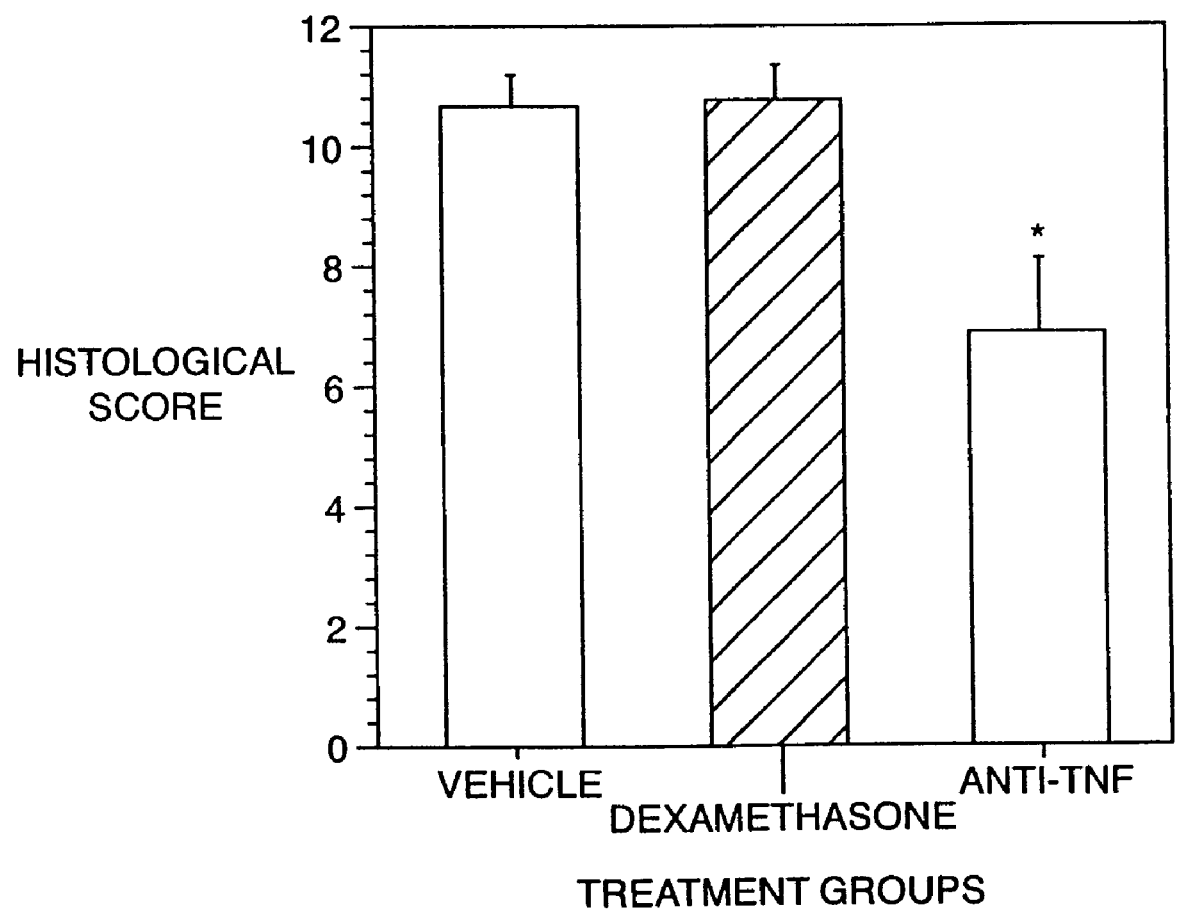
Figure 5D:
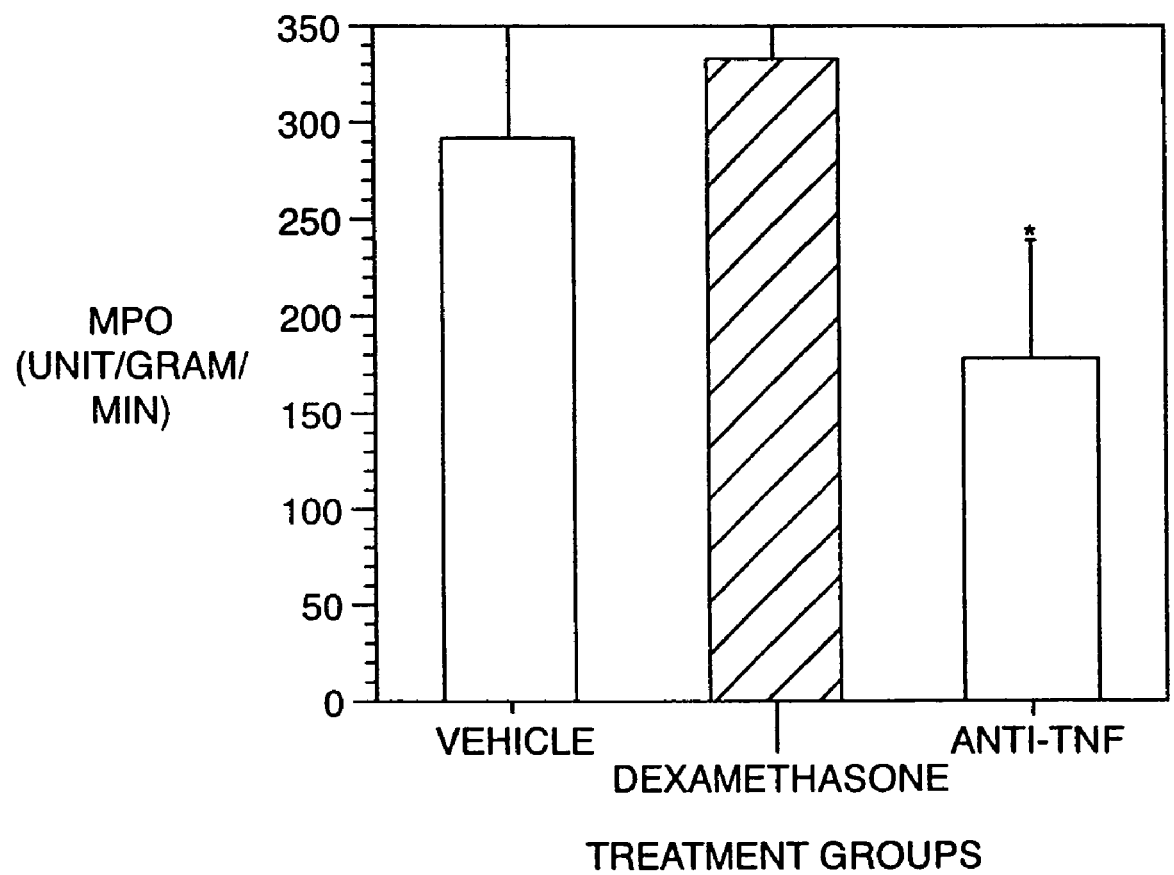

The present invention relates to therapeutic compositions and methods for the prevention treatment of IBD, and in particular the prevention and treatment of IBD in humans as well as other animals. The antibodies of the present invention have particular application to the prevention and treatment of Crohn's disease.

The present invention further teaches treatments comprising anti-cytokine antibody (and combinations of antibodies to cytokines) and compositions and methods used after the onset of symptoms of IBD. As noted above, the present invention also contemplates treatment comprising administering formulations comprising anti-cytokine antibody (e.g. anti-TNF, anti-IL-6, and/or anti-IL-12). In accordance with the present invention, such formulations are administered via intravenous, parenteral, rectal or oral route, although the present invention is not limited to these methods of administration.

It is not intended that the present invention be limited by the particular nature of a formulation or combination. The present invention contemplates combinations as simple mixtures as well as chemical hybrids. An example of the latter is where the receptor is covalently linked to a pharmaceutical such as a corticosteroid, or where two receptor types are covalently joined. Covalent binding can be accomplished by any one of many commercially available crosslinking compounds.

It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts. Unlike convention treatment approaches with drugs (e.g. steroids), treatment with the antibodies of the present invention do not run the risk (from a practical standpoint) of overdosing the patient. Excess antibody administered orally or rectally will simply pass through the treated subject.

Such compositions are typically prepared as sprays (e.g., intranasal aerosols) for topical use. However, they may also be prepared either as liquid solutions or suspensions, or in solid forms. Oral formulations (e.g., for gastrointestinal inflammation) usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%.

The compositions are also prepared as injectables, either as liquid solutions or suspensions; solid forms suitable for solution in, or suspension in, liquid prior to injection may also be prepared.

The antibodies of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

In a preferred embodiment, enteric formulations are employed, including but not limited to encapsulated antibodies. The terms "encapsuled" or "encapsulating" refers to the covering of a solid (e.g., lyophilized) form of antibody. The covering may comprise an enteric coating or a capsule. The terms "enteric coating" or "enteric film" are used interchangeably and refer to a material or compound which is resistant to acid pH (i.e., an acid-resistant compound), such as that found in the stomach. An enteric coating when applied to a solid inhibits the dissolution of the solid in the stomach.

Standard techniques are known to the art for the encapsulation of solid compositions. These techniques include microencapsulation of a solid composition wherein an enteric coating is applied to the solid composition. The coated material may be delivered orally to a subject by suspending the microencapsulated particles in pharmaceutical suspension solutions known to the art.

When a solid antibody is to be encapsulated using an enteric coating, the enteric coating may be applied using a one step coating process in which the enteric film is directly applied to the solid antibody; the coated antibody is said to be overcoated with the enteric film. Alternatively, a two step coating process may be employed wherein the solid antibody is first used to overcoat a non-pariel (i.e., a sugar particle of about 40-60 mesh size) and then the antibody-coated non-pariel is overcoated with the enteric film. Desirable enteric coatings for the delivery of antibody include polymethacrylates such as Eudragit® L30D (Röhm Tech, Inc.)

Solid antibody may formulated for oral delivery by insertion of the desired quantity of antibody into a capsule; the capsule would preferable have the characteristic of being resistant to dissolution in the stomach and being capable of dissolving in the intestines. Numerous suitable capsule formulations are available to the art; in addition standard techniques are available for the filling of capsules including the use of inert filler materials to provide sufficient bulk of the filling of a capsule with a therapeutic composition in a solid form. In addition to the use of microencapsulated antibody, the solid antibody may be delivered orally in tablet or pill form. The solid antibody may be combined with inert materials to provide sufficient bulk for the pressing of the tablet or pill. Once formed, the tablet or pill may then be coated with an enteric film to prevent dissolution in the stomach and to enhance dissolution in the intestines.

EXPERIMENTAL

The following examples serve to illustrate certain preferred embodiments and aspects of the present invention and are not to be construed as limiting the scope thereof.

Example 1

Production of Antibodies to TNF, IL-6, IL-8, and IL-12 Homodimer and Heterodimer in the Hen This example involved (a) preparation of the immunogen and immunization, (b) purification of anti-TNF, anti-IL-6, and IL-8 and anti-IL-12 (homodimer and heterodimer) chicken antibodies from egg yolk (IgY), and (c) detection of specific antibodies in the purified IgY preparations.

(a) Preparation of the Immunogen and Immunization.

Recombinant human (rH) Tumor Necrosis Factor Alpha, (TNF), recombinant human Interleukin 6, (IL-6), recombinant human Interleukin 8, (IL-8) and recombinant mouse Interleukin 12 homodimer or heterodimer was purchased (lyophilized without bovine serum albumin (BSA) and designated carrier-free) from R&D Systems Inc., Minneapolis, Minn. and produced in E. coli. TNF and interleukins 6 and 12 are considered proinflammatory cytokines. Active TNF exists as three TNF molecules forming a trimer. The native form of IL-12 exists as a heterodimer containing 2 distinct subunits designated as p30 and p40. Reports have indicated that the p40 subunit is the binding domain of the heterodimer and antibodies against only this subunit may be required to neutralize the native IL-12. (Gillessen S, et al. Eur J Immunol 1995; 25:200-206). The p40 subunit can form a dimer termed the IL-12 homodimer. Experiments using the p40 subunit were preformed because this form may be easier to prepare recombinantly compared to the heterodimer. Interleukin-8 is a class of chemotatic cytokines termed chemokines. The lyophilized cytokines and chemokines were reconstituted in phosphate-buffered saline pH 7.2-7.5 (PBS) at 50 ug/ml and from 2-10 ug of TNF was used to immunize each hen. Each hen received one 0.5 ml sub-cutaneous injection containing the individual cytokine with 75 ug Quil A adjuvant (Superfos Biosector, Denmark, distributed by Accurate Chem., Westbury, N.Y.) in PBS. The hens were immunized every 2 weeks for at least 3 times then placed on a maintenance immunization schedule where the hens were immunized every 4-6 weeks.

(b) Purification of Anti-cytokine Chicken Antibodies from Egg Yolk (IgY).

Groups of eggs were collected per immunization group at least 3-5 days after the last booster immunization. The chicken yolk immunoglobulin (IgY) was extracted by a two-step polyethylene glycol (PEG) 8000 method performed according to a modification of the procedure of Polson et al., Immunol. Comm., 9:495 (1980). The yolks were separated from the whites and the yolks were placed in a graduated cylinder. The pooled yolks were blended with 4 volumes of PBS and PEG was added to a concentration of 3.5%. When the PEG was dissolved, the protein and lipid precipitates that formed were pelleted by centrifugation at 9,000×g for 15 minutes.

The supernatants were decanted and filtered through 4 layers of gauze to remove the floating particulates and a second PEG step was performed by adding PEG to a final concentration of 12% (the supernatants were assumed to contain 3.5% PEG). After a second centrifugation, the supernatants were discarded and the IgY pellets were resuspended in PBS at approximately ⅙ the original yolk volume. IgYs extracted from the eggs of immunized hens are designated as "immune IgY," while IgYs extracted from the eggs of unimmunized hens is designated "preimmune IgY." The concentration of the fractionated IgY's were estimated by measuring the absorbance at 280 nm (an optical density at 280 nm of 1.3 equals 1 mg of IgY/ml. The antibody concentrations were about 20-30 mg/ml.

(c) Detection of Anti-cytokine Antibodies in the Purified IgY Preparations.

In order to determine if anti-cytokine response was generated and to determine relative levels of the response, enzyme-linked immunosorbent assays (ELISA) were performed. Briefly, ninety-six well Falcon Pro-bind micro-titer plates were coated overnight at 40C with 100 ul/well with different cytokines (TNF, IL-6, IL-12 homodimer or heterodimer and IL-8) at 0.1-1.0 ug/ml PBS. The wells are then blocked with PBS containing 1% BSA and 0.05% Tween 20 and incubated for about 1 hour at 370C. The blocking solution was removed and the immune or preimmune IgY was diluted in PBS containing BSA and the plates were incubated for 1 hour at 370C. The plates were washed 3 times with PBS containing 0.05% Tween 20 and three times with PBS alone. Alkaline phosphatase-conjugated anti-chicken IgG was diluted 1:1000 in PBS containing 1% BSA and 0.05% Tween 20, added to the plates and incubated 1 hour at 370C. The plates were washed as above and p-nitrophenyl phosphate at 1 mg/ml in 0.05 M Na2CO3, pH 9.5, 10 mM MgCl2 was added. The plates were read in a Dynatech plate reader at 410 nm about 30 minutes after substrate addition. Good antibody titers (reciprocal of the highest immune IgY generating a signal about 3-fold higher than that of preimmune) ranging from 10,000 to 50,000 was generated.

The level of antibody response in the hens against all the cytokines tested were very good. Given the low amounts of antigen used for immunization, indicates cytokines may be very immunogenic in the hens and the avian system is a well-suited method to generate anti-mammalian cytokine antibodies.

Example 2

Determination of Anti-TNF IgY Neutralizing Ability in a Cell-based Neutralization Assay This example involved the testing of the anti-TNF IgY neutralizing ability in a cell-based neutralization assay and comparing the activity to a commercial anti-TNF monoclonal antibody.

Bioactivity of the anti-TNF IgY antibody was evaluated in the murine L929 cell based neutralization assay as previously described (Mathews N., et al 1987, Lymphokines and Interferons). Briefly, murine L929 cells (ATCC, Rockville, Md.), sensitive to the cytotoxic effects of recombinant human TNF (rhTNF), were grown in sterile conditions with Ham's F12 and Dulbecco's Modified Eagles media (1:1 vol:vol ratio), containing 1.2 g/L sodium bicarbonate and 15 mM Hepes (Life Technologies, Gaithersburg, Md.) and supplemented with 10% fetal bovine serum (Life Technologies). Cells were harvested using trypsin:EDTA (Life Technologies), and 2×10⁴ cells were dispensed into each well of a 96-well flat-bottomed plate (Costar) and incubated for 20 hours in a humidified chamber at 37 C and 5% CO2. In a separate plate, anti-TNF IgY, Remicade, (a commercial mouse monoclonal antibody to human TNF, Centocor, Malvern, Pa.) as a positive control, and a preimmune antibody, served as a negative control.

The IgY's were serially diluted in PBS (Life Technologies) supplemented with 1% BSA (wt:vol)(Life Technologies) and 10 ug/ml actinomycin D (ICN, Costa Mesa, Calif.). To each well containing antibody, an equal volume of 1 ng/ml rhTNF (R&D Systems, Minneapolis, Minn.) was added, including controls which received only rhTNF or only PBS diluent. The plate was then incubated for 1 hour at 37 C. Finally, the antigen-antibody mixture was added to the cells and incubated for 20 hours at 37 C., 5% CO2 in a humidified chamber. Cell viability was measured using the chromogenic Cell Titre 96 Proliferation Assay (Promega Corporation, Madison, Wis.) recording the optical density at 490 nm. The amount of anti-TNF that resulted in the prevention of cell death in 50% and 90% of the cells, termed neutralization dose 50 and 90 (ND50 and ND90) was calculated for each antibody.

FIG. 1 shows results of the cell based TNF neutralization assay. Anti-TNF IgY had an ND50 and ND90 of 70 ng/ml and 142 ng/ml respectively, and the positive control antibody, Remicade, had an ND50 and ND90 of 140 ng/ml and 10,900 ng/ml respectively. The concentration labeled on the x-axis is based on total IgY content for the anti-TNF IgY, and is a measure of specific monoclonal antibody for the Remicade. The preimmune IgY did not show any significant neutralization of TNF in this assay. This study indicates that the neutralizing activity of the anti-TNF IgY is significantly better than that of mouse monoclonal, Remicade. Despite only a two-fold difference between the ND50's of the two antibodies, there was almost a hundred fold difference in the ND90's. The Remicade did not achieve 100 percent neutralization, even at the highest concentration tested Example 3

Determination of Anti-IL-6 IgY Neutralizing Ability in a Cell-based Neutralization Assay This example involved the testing of the anti-IL-6 IgY neutralizing ability in a cell-based neutralization assay.

To measure the ability of the anti-IL-6 IgY to neutralize the bioactivity of rhIL-6, a standard IL-6 cell assay was performed. B9 cells (The Central Laboratory, Amsterdam, The Netherlands) and rhIL-6 were incubated with various concentrations of the antibody (100 ug/ml-0.2 ug/ml) for 1 hour at 37 C and 5% CO2, in a 96 well plate. As a positive control, a commercially available anti-IL-6 antibody (R&D Systems) were used, and as a negative control, preimmune IgY antibodies were used. All antibodies and antigens were diluted in RPMI 1640 (Life Technologies) with 5% fetal bovine serum (Life Technologies), and 50 (M 2-mercaptoethanol. The assay mixture, containing antibodies at the concentrations listed, rhIL-6 (R&D Systems) at 2.5 ng/ml, and cells at 1×105 cells/ml, was incubated at 37 C and 5% CO2 for 48 hours. For the last 2 hours of the incubation, Cell Titre 96 Proliferation Assay (Promega Corp.) was added, and the optical density of the plate was read at 490 nm. The ND50 of the anti-IL-6 IgY was about 10 ug/ml. (Data not shown.)

Example 4

Determination of Anti-IL-8 Neutralizing Ability in a Cell-based Neutralization Assay This example involved the testing of the anti-IL-8 IgY neutralizing ability in a cell-based neutralization assay.

To assess the neutralization capacity of the anti-IL-8 IgY antibodies a standard assay to measure IL-8 activity was performed. IL-8 can induce myeloperoxidase activity measured from human neutrophils, as previously described (Schroder, J., et al, J. Immunol., 139:3474-3483,1987). Human neutrophils were isolated from whole blood and treated with 5 ug/ml of cytochalasin B (Sigma). To various concentrations of anti-IL-8 IgY antibody (7.6 mg/ml-0.95 mg/ml), rhIL-8 (R&D Systems) at 1 ug/ml was added in Gey's buffer (Sigma) with 1 mg/ml BSA (Sigma) and incubated for 30 minutes at room temperature in a 96 well plate. As a positive control, commercially available anti-IL-8 (R&D Systems) was used, and as a negative control, preimmune IgY antibodies were used. To each experimental well, 7×106 cells/ml were added to a final volume of 100 ul and incubated with the antibody-antigen mixture for one hour at room temperature. Supernatants were harvested, and myeloperoxidase activity was measured using 0.167 mg/ml o-dianisidine (Sigma), with 0.0005% hydrogen peroxide in a 50 mM phosphate buffer, pH 6.0. The highest concentration of anti-IL-8 IgY tested, neutralized approximately 28% of the bioactivity of the rhIL-8. (Data not shown).

Example 5

Determination of Anti-IL-12 (Homodimer and Heterodimer) Neutralizing Ability in a Cell-based Neutralization Assay This example involved the testing of the anti-IL-12 homodimer and heterodimer IgY neutralizing ability in a cell-based neutralization assay.

To measure the ability of anti-IL-12 IgY (generated to the heterodimer isoform) to neutralize the bioactivity of rhIL-12 heterodimer a cell-based assay was performed using peripheral blood mononuclear cells, (PBMC's). PBMC's were purified and activated according to the procedure in Current Protocols in Immunology, Vol. 1 section 6.16, 1994. Various concentrations of the anti-IL-12 IgY (2,500 ug/ml-0.032 ug/ml) were incubated with rhIL-12 (R&D Systems) at 1 ng/ml for 1 hour at 37(C in a 96 well plate. All dilutions were performed in the assay medium which consisted of a 1:1 dilution of RPMI (Life Technologies) and Dulbecco's Modified Eagles Medium (Life Technologies) with L-arginine (Life Technologies) at 2.5 mg/ml, 10% D-glucose (Sigma), and 10% human serum (Irvine Scientific). As a positive control, a commercially available anti-IL-12 (R&D Systems) was used, and as a negative control, preimmune IgY antibodies were used. Following the preincubation, the PBMC's were added to the antigen-antibody mixture at a final concentration of 2×105 cells/ml and incubated for 48 hours at 37(C with 5% CO2. During the final two hours of the incubation, Cell Titre 96 Proliferation Assay (Promega Corporation) was added, and the optical density was read at 490 nm. The ND50 for the anti-IL-12 heterodimer IgY was measured at 0.47 mg/ml. (Data not shown).

The same assay was performed using the IgY antibodies generated to the homodimer form of IL-12. Antibodies against the homodimer, based on the literature, may have been effective at neutralizing the IL-12 heterodimer. However, these antibodies, even at very high concentrations, did not demonstrate the ability to neutralize the bioactivity of IL-12 on PBMC's (Data not shown.)

Example 6

Testing of Anti-TNF IgY Efficacy in a Crohn's Animal Model

A published animal model of Crohn's disease was used to characterize the efficacy of anti-TNF IgY in either preventing or treating acute inflammation or in accelerating the healing process in chronic inflammation. (Sartor R. B., Ailment Pharmacol Ther 1997; 11:89-97). A chemically-induced disease model described by Morris G. P., et al. Gastroenterology 1995; 96:795-803 was employed. This example involves a) description of establishment of the Crohn's model b) Description of assessment methods to determine efficacy: colonic morphological evaluation, histological evaluation, biochemical evaluation, c) Prevention and treatment during the acute stage of colitis, d) treatment during the chronic phase of colitis.

a) Description of Establishment of the Crohn's Model.

The TNBS-induced rat colitis model of Crohn's disease uses the hapten trinitrobenzenesulfonic acid (TNBS) administered rectally to induce colonic ulceration and transmural inflammation. The TNBS is thought to modify proteins of host tissues, inducing a delayed-type hypersensitivity reaction [Elson C. O. et al., Gastroenterology 1995:109:1344-1367]. A single enema of TNBS can result in granulomas and bowel thickening that can persist for 3-8 weeks. This reaction induces many of the histopathological and clinical features of human Crohn's disease, and responds predictably to drugs used in treating IBD [Elson C. O. et al.]. This model can be used as an acute or a chronic colitis model. The chronic phase of the disease is characterized by the absence of neutrophils at the site of inflammation. In the acute model, treatments are initiated either before or shortly after the TNBS challenge, whereas in the chronic model treatments can begin several weeks after challenge. Sprague-Dawley rats (Charles River) at 200-225 grams were given a TNBS (Fluka) enema using an 8 cm, 14 gauge feeding needle. TNBS was prepared by dissolving 30 mg of TNBS in 0.25 ml of 50% ethanol. TNBS-treated rats developed diarrhea and display profound weight loss within 24 hours.

b) Description of Assessment Methods to Determine Efficacy.

Colonic Morphological Evaluation:

After antibody treatment the terminal 6-7 cm of terminal colon was removed, cut open longitudinally, cleaned of fecal material, and weighed. The colon segment was placed flat, lumen side-up, on a Styrofoam block and pinned. Colonic inflammation and damage was macroscopically evaluated and scored using a scale described by Morris G. P., et al. Gastroenterology 1995; 96:795-803.

Criteria for Scoring Gross Morphologic Damage using TNBS:

No damage.
Localized hyperemia, but no ulcers.
Linear ulcers with no significant inflammation.
Linear ulcer with inflammation at one site.
Two or more sites of ulceration and/or inflammation.
Two or more major sites of inflammation and ulceration of one major site of inflammation and ulceration extending>1 cm along the length of the colon.

Raw scores were combined in each group, and the mean and SEM were calculated.

Histological Evaluation:

After treatment the terminal colonic segment pinned to the Styrofoam block was fixed in phosphate-buffered 10% formalin, luminal side down. The entire fixed segment was embedded in paraffin on edge and cut longitudinally to reveal the full-depth of the colonic morphology. The cut sections were stained with hematoxylin and eosin (H&E), and microscopic histological assessment was performed in a blinded fashion on coded slides. The histologic scoring system used was described by Elson C. O., J Immunol 1996; 157:2174-2185.

Histologic scoring system for evaluation of colonic inflammation using TNBS

| | | |
|---|---|---|
| Extent | 0 | None |
| | 1 | Focal |
| | 2 | Limited to one segment |
| | 7 | Involving more than one segment |
| Inflammation | 0 | None |
| | 8 | Mild |
| | 9 | Moderate |
| | 10 | Severe |
| Damage | 0 | None |
| | 11 | Mild (superficial) |

-continued

| | | |
|---|---|---|
| | 12 | Moderate (involving muscularis mucosa) |
| | 13 | Severe (transmural) |
| Regeneration | 3 | None |
| | 14 | Focal migration and mitotic figures |
| | 15 | Broad, multifocal re-epithelialization |
| | 16 | Complete re-epithelialization |

Biochemical Evaluation:

A biochemical method to assess severity of inflammation was performed as described by Krawisz, J. E., et al. Gastroenterology 1984; 87:1344-1350. This method determines colonic myeloperoxidase (MPO) activity as a quantitative indicator of neutrophil activity. Before tissue fixation, a representative segment of the colon was removed, suspended in 0.5% hexadecyltrimethylammonium bromide (HTAB) in 50 mM phosphate buffer pH 6.0, and placed on ice. The segments were freeze-thawed once and homogenized using a Tissue Tearor (Biospec Products) for 45 seconds on ice, and then freeze-thawed again. To measure MPO activity, 50 ul of sample was added to 1 ml of substrate solution (0.167 mg/ml o-dianisidine and 0.0005% hydrogen peroxide in 50 mM phosphate buffer pH 6.0). The change in absorbance at 460 nm was read over 1 minute in a spectrophotometer (Hewlett-Packard). One unit of MPO activity is defined as that degrading 1 umol of peroxide per minute at 25° C. Raw scores were combined in each group, and the mean and SEM were calculated.

c) Acute Treatment Studies.

A five day treatment with IgY or vehicle was started either 24 hours before TNBS challenge or 48 hours post-TNBS challenge. Anti-TNF dose response studies at 7.5, 30 or 120 mgs/day in 200 gram rats administered orally 48 hours post-TNBS challenge indicated that the highest dose was most effective against TNBS-induced colitis. In subsequent experiments, rats were given 100-120 mgs/day (500 mg/kg/day) of anti-TNF IgY or IgY from unimmunized (preimmune) hens as a control per day given in two, 50-60 mg doses, b.i.d. Vehicle (IgY diluent) treated rats were given 0.1M carbonate buffer pH 9.3-9.5. IgY's were diluted in high pH buffer to overcome the acidic conditions of the stomach and prevent degradation. Animals were orally dosed using a 5 cm, 18 gauge feeding needle (Popper and Sons) with 2 mls of IgY. In comparator drug studies, rats were given doses reported as efficacious [Fitzpatrick L. R., et al. Agents Actions 1990:3-4:393-402.] for chemically-induced colitis. Treatments of 100 mg/kg, b.i.d. of sulfasalazine (Sigma) or 1 mg/kg , b.i.d. of dexamethasone (Sigma) were given for 5 days. The comparator drugs were prepared in a buffer with 0.5% methylcellulose (MC) (Sigma) as described [Fitzpatrick et al.]. For consistency the IgY preparations in the comparator studies also contained 0.5% MC. During treatment the rats were weighed daily. After 5 days of treatment, groups of control and drug-treated rats were sacrificed, and colons removed for evaluation. Seven to nine animals were used per group in each experiment.

FIGS. 2A through 2D, show results of the dose response study in the TNBS-challenged rats treated with vehicle or different concentrations of anti-TNF IgY. The rats were treated approximately 48-hours post-TNBS challenge. The results of percent change in total body weight, (FIG. 2A), colon weights, (FIG. 2B), histology score, (FIG. 2C), and MPO activity (FIG. 2l), demonstrate a dose-dependant effect of the anti-TNF IgY.

FIGS. 3A through 3D, show results after pre-challenge treatment with vehicle, preimmune IgY, or anti-TNF IgY. Colon weights (FIG. 3A), colon damage scores (FIG. 3B), histology scores (FIG. 3C), and MPO activity (FIG. 3D) were compared. Normal controls (no TNBS treatment) are also compared in several figures. Results described in the figure legends indicate that anti-TNF IgY significantly reduced TNBS-induced colitis in all assessment parameters.

FIGS. 4A through 4D, show results after post-challenge (48 hours) treatment with vehicle, sulfasalazine, or anti-TNF IgY. Colon weights (4A), colon damage scores (FIG. 4B), histology scores (FIG. 4C), and MPO activity (FIG. 4D) are compared. Results described in the figure legends indicate that anti-TNF IgY significantly reduced TNBS-induced colitis in all assessment parameters.

Gross morphology of the lower rat colon after post-challenge treatment with vehicle, sulfasalazine or anti-TNF IgY was examined (data not shown). Anti-TNF IgY reduced TNBS-induced gross inflammation in the rat colon. The anti-TNF treatment was more effective than sulfasalazine at the dose tested.

Microscopic histological results from representative colon segments after post-challenge treatment with vehicle, sulfasalazine, and anti-TNF IgY were also compared (data not shown). These results indicate that treatment with anti-TNF IgY significantly reduced TNBS-induced histological damage. The treatment with anti-TNF IgY was more effective than sulfasalazine at the dose tested.

FIGS. 5A through 5D, show results after pre-challenge treatment with vehicle, dexamethasone, or anti-TNF IgY. Colon weights (FIG. 5A), colon damage scores (FIG. 5B), histology scores (FIG. 5C), and MPO activity (FIG. 5D) are compared. Results described in the figure legends indicate that anti-TNF IgY is statistically more effective at preventing TNBS-induced colitis in all assessment parameters. Both anti-TNF IgY and dexamethasone treatment significantly reduced total colon weight compared to vehicle treatment. However, the anti-TNF treatments were much more effective than dexamethasone in preventing colonic damage and neutrophil infiltration.

d) Chronic Treatment Studies.

A five day treatment b.i.d. of anti-TNF IgY, preimmune (PI) or vehicle (0.1 M carbonate buffer pH 9.3-9.5) was orally administered as described above except treatments were started 17 days after TNBS challenge.

Figure 6A:
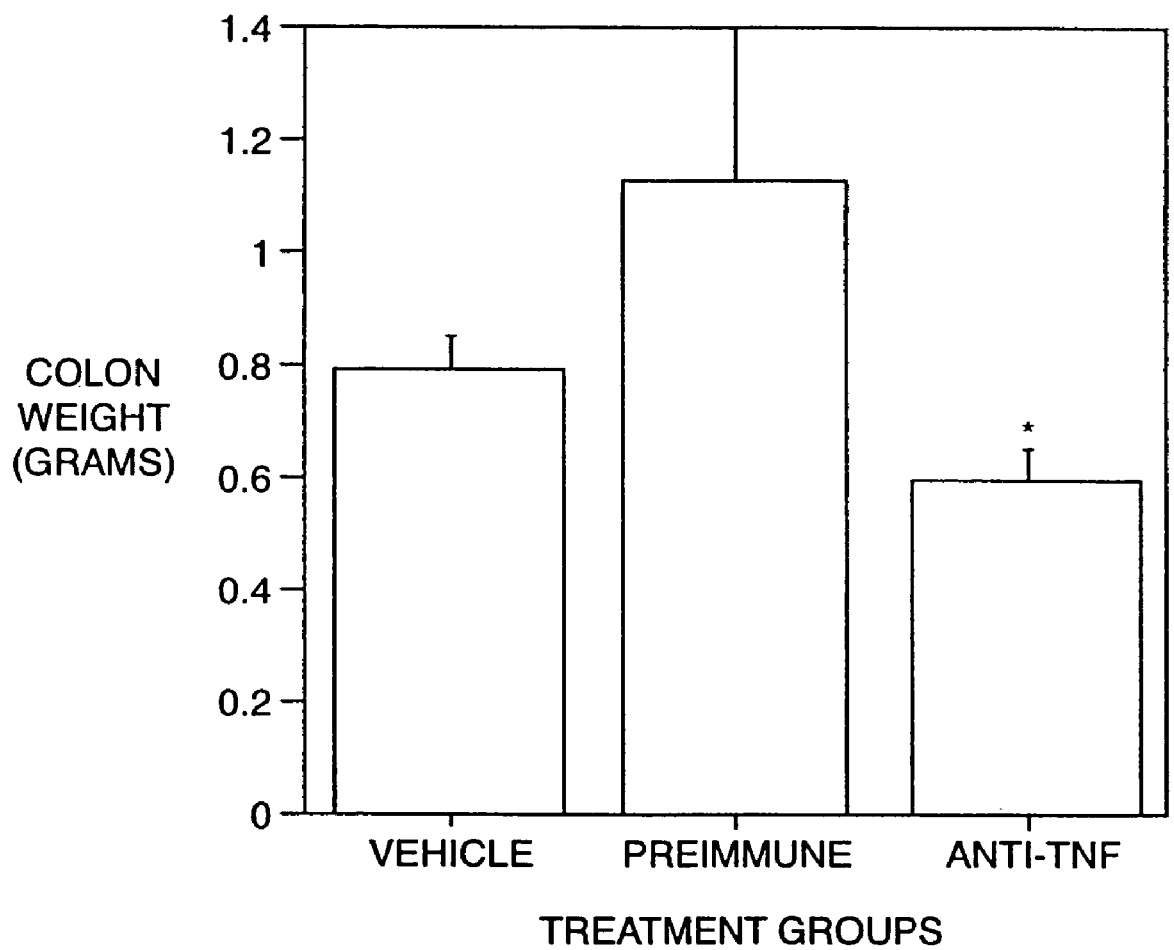
FIGS. 6A through 6C are bar graphs showing the results of anti-TNF treatment started 17 days after initiation of an inflammatory reaction in a rat model for IBD.
Figure 6B:
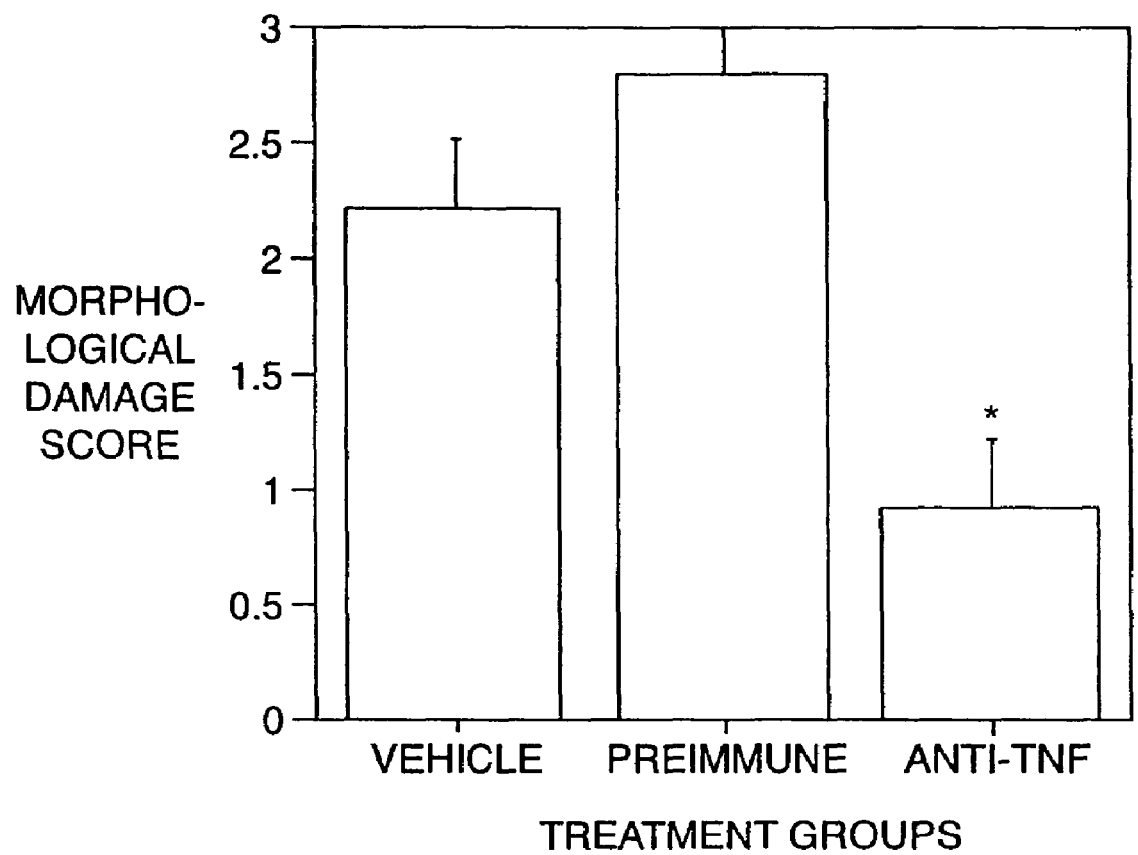
Figure 6C:
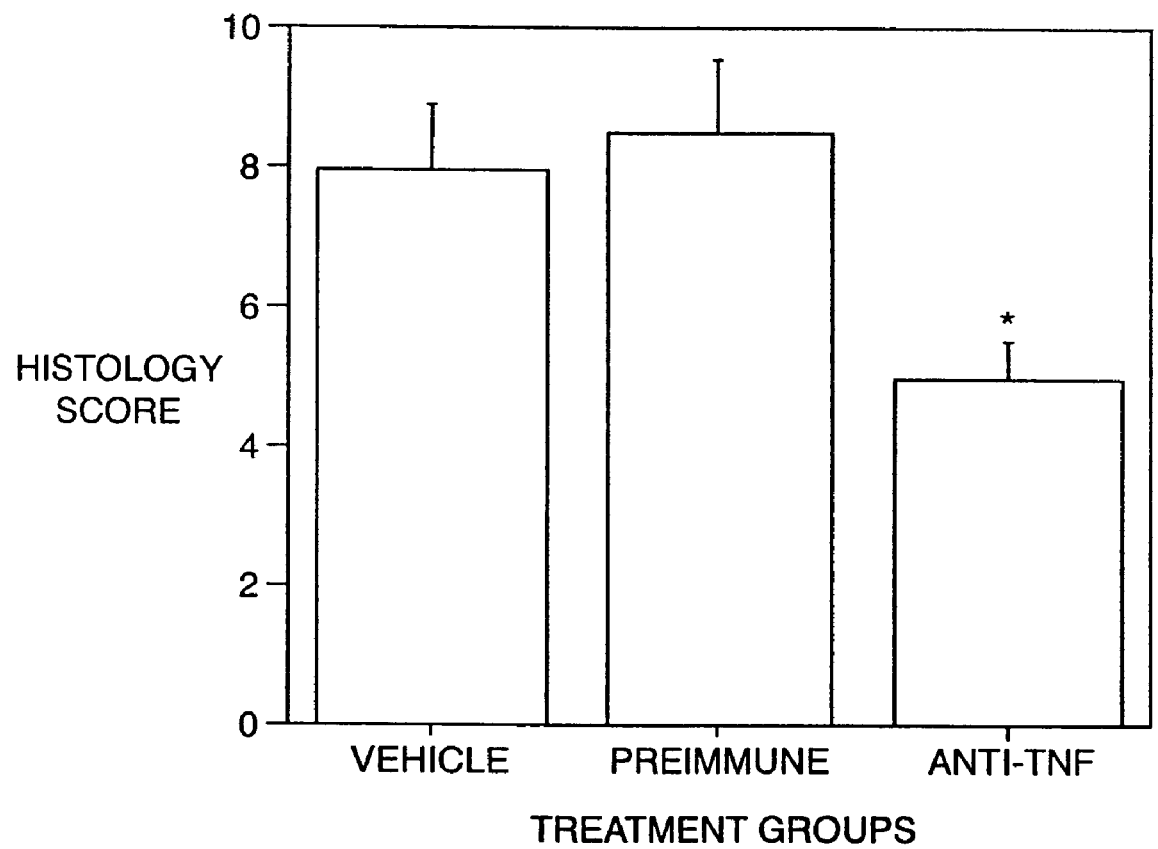

FIGS. 6A through FIG. 6C show results of anti-TNF treatment started 17 days after TNBS challenge. Results described in the figure legends indicate that anti-TNF IgY is statistically effective at treating TNBS-induced colitis during the chronic stage compared to PI-treated or vehicle-treated animals in all assessment parameters. Colon weights (FIG. 6A), colon damage scores (FIG. 6B), histology scores (FIG. 6C) in all three treatment groups were compared.

Example 7

Immunohistochemistry Studies to Determine the Location of Anti-TNF IgY and TNF in Colonic Sections This example involves (a) Determination of the site of anti-TNF IgY in colonic sections and (b) Determination of the site of endogenous TNF in colonic sections a) Determination of the Site of Anti-TNF IgY in Colonic Sections.

To determine the site of action of the applied antibodies, tissue sections were procured and analyzed from TNBS treated animals early in the inflammatory process. Each animal received two treatments with antibody or control. The slides were deparaffinated in toluene and rehydrated with descending ethanol concentrations. To inhibit endogenous biotin background, sections were incubated in 1.5 ug/ml of ExtrAvidin (Sigma, St. Louis, Mo.) for 30 min at room temperature. This was followed by blocking in 1% gelatin in PBS for 30 minutes at room temperature. The primary antibody was a biotin labeled anti-chicken IgG specific for the heavy chain (Cortex Biochem, San Leandro, Calif.) diluted to 10 ug/ml in PBS containing 2% normal rat serum, incubated for 1 hour at room temperature. After washing the sections in PBS, there was a 1 hour incubation with a 1:1,000 dilution of alkaline phosphatase labeled ExtrAvidin (Sigma). Specific binding was determined after applying BCIP/NBT (KPL, Gaithersburg, Md.) as a substrate and microscopically localizing the stain.

b) Determination of the Site of Endogenous TNF in Colonic Sections

Immunohistochemistry was also performed to identify the location of TNF in the colonic sections of TNBS treated animals following a full treatment regimen. The procedure was performed as described above except goat anti-TNF (R&D Systems, MN) at 10 ug/ml was applied as the primary antibody, followed by a biotinylated anti-goat IgG (Vector Laboratories, Inc., Burlingame, Calif.) at 10 ug/ml in 2% rat serum as the secondary antibody.

Microscopic histology was done to identify IgY within the TNBS treated rat colon of both experimental and control tissues. Vehicle treated, preimmune treated, anti-TNF IgY treated, and normal control tissues were compared. IgY was found in the mucosa and submucosa near ulcerated areas of the anti-TNF treated sections (data not shown). The presence of detectable IgY was not seen in the vehicle treated (as expected) or preimmune treated rats. Such studies by the inventors indicates that TNF can be readily identified in the ulcers of vehicle treated animals, but much less so in the ulcers of anti-TNF IgY treated animals (data not shown). The normal control shows a small population of staining cells in the very tips of the crypts (data not shown).

Example 8

Anti-TNF IgY Efficacy in a Ulcerative Colitis (UC) Animal Model

A published animal model of UC disease was used to characterize the efficacy of anti-TNF IgY. A chemically-induced UC model induced by dextran sodium sulfate (DSS) described by Okayasu et al. Gastroenterology 98:694-702 (1990) was employed. This example involves a) description of establishment of the model b) description of assessment methods: prevention of mortality, hemoccult testing, histological evaluation and biochemical evaluation c) acute treatment studies d) chronic treatment study.

a) Description of Establishment of the UC Model

In order to determine whether anti-TNF polyclonal avian antibodies are capable of neutralizing UC-like disease, a well-characterized and accepted murine model of UC was utilized using dextran sodium sulfate (DSS). This model simulates UC, and the colitis induced by DSS is characterized by ulceration of the colonic mucosa, blood in the stool and weight loss. Both acute and chronic colitis can be induced in this model. The DSS is administered in the drinking water to mice. Acute colitis in mice occur within several days during the initial DSS treatment cycle, while chronic UC occurs after prolonged administration of DSS during several cycles.

The mice present with bloody diarrhea, gross rectal bleeding, and weight loss either during DSS treatment or within days after treatment. Some strains of mice, such as C3H/HeJ mice or Swiss Webster mice, are very sensitive to DSS treatment, resulting in a high rate of mortality from UC [Mahler M. et al. 1998 Amer J Physiol]. Strains less sensitive to DSS such as CBA/J display severe colitis with less mortality. The mode of action of DSS is unknown, but it is thought to alter the permeability of the intestinal mucosa. Signs of acute colitis in sensitive mice can occur during the first treatment. Chronic ulcerative colitis can be induced by 3 to 5 cycles of administration of DSS, in which each cycle consists of 5-7 days of DSS treatment followed by 7-10 days of drinking unaltered water.

Swiss Webster mice (8-9 week old) from Charles River and C3H/HeJ or CBA/J mice (8-9 week old) from Jackson Labs were treated with 3.5-5% DSS, 40,000 MW (ICN Biochemicals or TdB Consultancy AB) in distilled water for 5 to 7 days. IgY (anti-TNF IgY), control (preimmune IgY), or vehicle (phosphate-buffered saline [PBS] pH 7.2-7.4) was administered during or after DSS treatment. In acute treatment studies, mice were treated either during or immediately after one DSS treatment. In chronic treatment studies, mice were treated after three complete cycles (1 cycle=DSS treatment followed unaltered drinking water). Mice were given about 4 mg of IgY intrarectally in 100 ul of PBS, b.i.d., using a straight 18 gauge feeding needle. During the 5-6 days of treatment, mortality and presence of blood in the stools were noted. After treatment, the mice were sacrificed and 2-4 cm of terminal colon was removed for evaluation. Three to ten animals were used per group in each experiment.

b) Description of Assessment Methods to Determine Efficacy

Prevention of Mortality:

After a 7 day course of 5% DSS in a DSS hypersensitive mouse strain (C3H/HeJ), mortality from colitis was recorded during and after vehicle, Preimmune or anti-TNF IgY treatment.

Hemoccult Testing:

At various time points during and after drug treatment, the presence of blood in the stools (a distinct characteristic of UC) in mice was determined using a commercial assay for fecal blood (Hemoccult slide kit, SmithKline Diagnostics, Inc., San Jose, Calif.)

Histological Evaluation:

The 2-4 cm segment of mouse colon was fixed, processed, and stained with H&E as described in Example 3 (b). The proximal and distal portions of each colon segment were examined separately. The histology score was the sum of both. The histologic scoring system of Cooper H. S., et al., Lab Investigation 1993; 69:238-249. was used:

Histologic scoring system for evaluating colonic inflammation in DSS-induced colitis:

Normal.

No inflammation, shortening of crypts.

Loss of basal two-thirds of the crypts.

Loss of entire crypt with retainment of epithelium.

Inflammatory infiltration and ulceration.

Raw scores were combined in each group, and the mean and SEM were calculated.

Biochemical Evaluation:

The MPO assay as described in example 6(b) was used to assess severity of inflammation after treatment.

c) Acute Treatment Studies

Experiments were performed to determine if mice could be rescued from acute colitis lethality using avian anti-TNF. Previous work using a rat anti-mouse TNF monoclonal antibody (G. Kojouharoff, et al., Clin. Exp. Immunology 107: 353-358, 1997) or mouse anti-TNF polyclonal antibody (A. D. Olson, et al., J. Pediatric Gastroenterology and Nutrition 21: 410-418, 1995) administered parenterally failed to protect acute colitis induced by DSS in mice. The treatment regimen in this example was performed essentially as described by Kojouharoff et al. except, the anti-TNF was administered luminally via the rectum instead of intraperitoneally.

Figure 7:
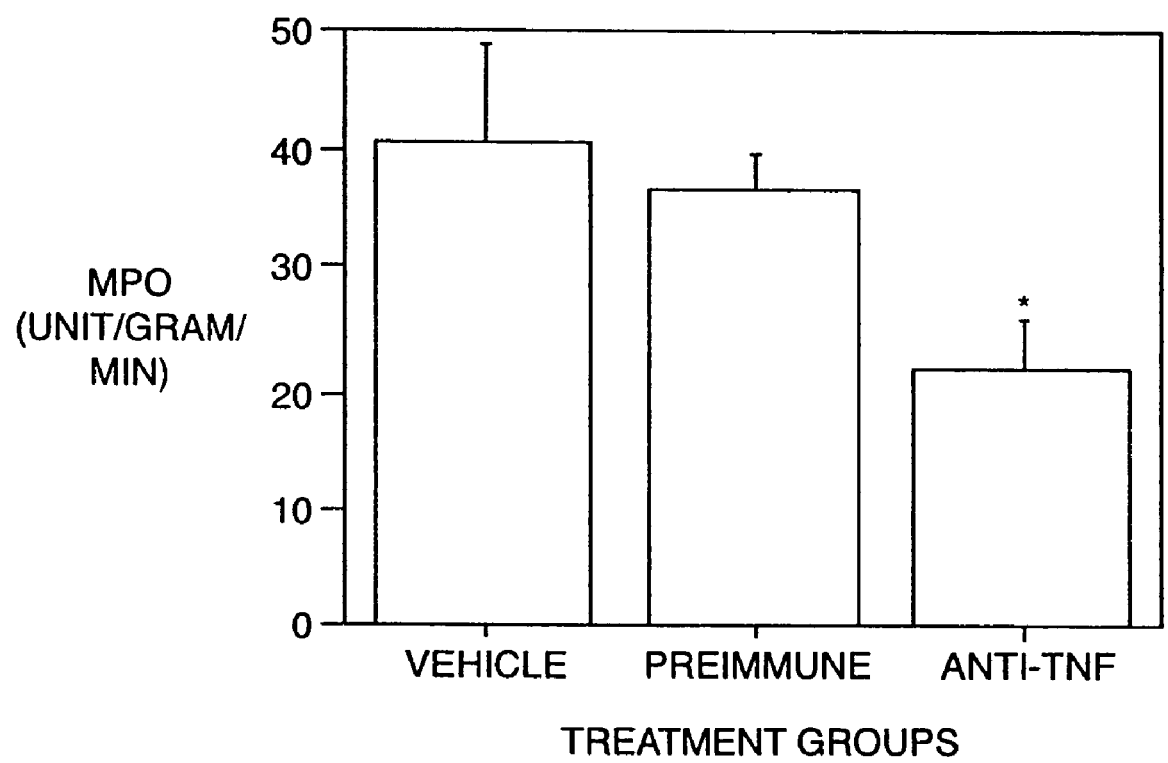
FIG. 7 is a bar graph showing MPO activity in colons of anti-TNF treated mice and survivors of preimmune and vehicle treated mice. Intrarectal delivery of anti-TNF antibodies beginning days 3 of a 7 day DSS treatment regimen significantly reduces tissue myeloperoxidase levels as compared to preimmune control (n=5, *p<0.05), but not the vehicle control (n=10, *p<0.2).

Briefly, for therapeutic purposes during acute colitis, mice were treated twice per day with 0.1 ml. of either anti-TNF alpha or preimmune IgY containing 2-4 mg. of IgY in PBS. The mice were treated rectally using a straight 20 gauge feeding needle (Popper & Sons Inc., New Hyde Park, N.Y.) and a 1 ml syringe after light anesthesia with ether. The mice were treated from day 3 to day 7 during the DDS administration. Untreated mice with DSS induced colitis served as controls. The ability of anti-TNF antibody to rescue mice from lethality associated with acute IBD is shown in Table 1. The percent of survival in each of the groups is shown 1 day after termination of DSS and antibody treatment. Note that the use of anti-TNF antibody resulted in a statistically significant increase in animal survival as compared to the untreated and Preimmune premix controls, with a 100% survival rate for the anti-TNF antibody administration as contrasted with the much lower 52% survival rate for the untreated animals, and 50% for the Preimmune controls. MPO activity was measured in colons of all anti-TNF treated mice and survivors of preimmune and vehicle treated mice. Anti-TNF treated mice showed a significant reduction in MPO activity compared to the control groups (FIG. 7).

The above experiment utilized DSS induced colitis positive mice and that were either untreated, or treated with a luminal (rectal) administration of preimmune or anti-TNF antibodies. The anti-TNF survival rate of 100% establishes conclusively a high increase in survival as compared with the 52% and 50% survival rates for both the untreated and Preimmune controls. The results of this experiment proves that avian anti-TNF antibody negates the lethal effect of IBD in vivo and strongly suggests that avian anti-TNF antibody will be useful in preventing or treating IBD.

Another experiment was performed to confirm the above results. The procedures used were similar, except that animal weight gain, incidence of diarrhea and presence of blood in the stool using a Hemoccult assay (Smith Kline Diagnostics, Inc., San Jose, Calif.) were monitored in addition to survival rate.

The kinetics of body weights of mice with acute colitis in the treatment groups is shown in FIG. 9. In contrast to the untreated and preimmune-treated mice, body weights were generally higher and increased most rapidly in the anti-TNF treated mice. Interestingly, weight gain in mice treated parenterally with anti-TNF was reported to be severely delayed after the end of DSS feeding (see G. Kojouharoff, et al., Clin. Exp. Immunology, cited above).

Three days after the termination of DSS-treatment, stool samples were collected from mice without obvious bloody diarrhea from each group and a Hemoccult test was performed to determine blood in the stool. The results are shown in Table 2. The Hemoccult assay was not performed on mice with obvious bloody stools. These mice and mice with bloody diarrhea that died prior to the Hemoccult testing were considered Hemoccult positive and included in Table 2. The results indicate that anti-TNF IgY effectively prevented blood stools during acute colitis by DSS. In contrast, a previous report (see A. Olson et al.) indicated that anti-TNF serum administered intraperitoneally did not prevent the appearance of blood in the stool of DSS-treated mice.

Table 3 results demonstrate that anti-TNF IgY can effectively prevent mortality and morbidity (diarrhea) in the mice during acute colitis by DSS. The survival rate three days after the termination of DSS treatment in the anti-TNF treated mice was 93%, while survival rates for untreated and preimmune treated mice were 53% and 31%, respectively. In addition, diarrhea was significantly reduced in the anti-TNF treated mice compared to the untreated and preimmune-treated mice. Diarrhea was present in 87% and 92% of the untreated and preimmune treated mice (respectively) while only 21% of the anti-TNF treated mice were afflicted. The results of these treatment studies during acute colitis using DSS in mice demonstrates that luminally delivered anti-TNF antibody is an effective therapy against IBD.

Another acute DSS study was performed whereby C3H/HeJ mice were treated rectally with anti-TNF, vehicle, or preimmune immediately following a single five day cycle of 5% DSS.

Figure 8A:
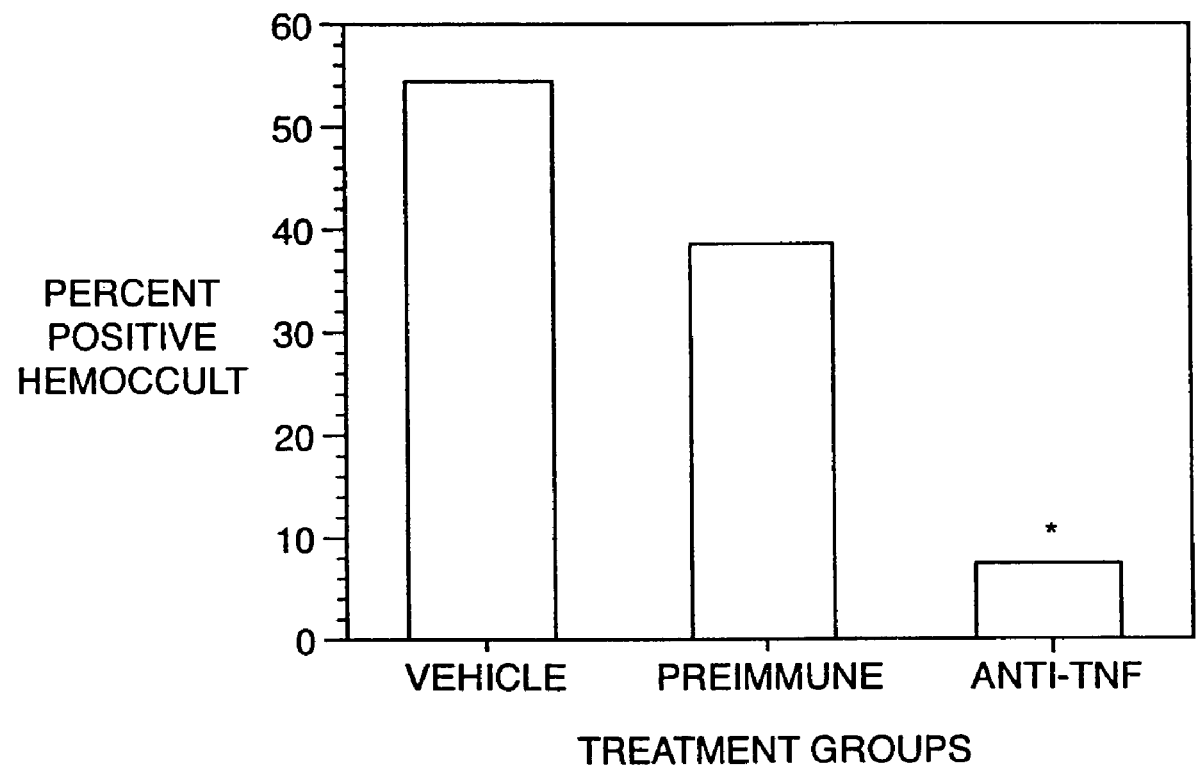
FIGS. 8A through 8C are bar graphs showing the treatment results in a mouse model (C3H/HeJ mice) of IBD involving treatment rectally with anti-TNF, vehicle, or preimmune immediately following a single five day cycle of 5% DSS.
Figure 8B:
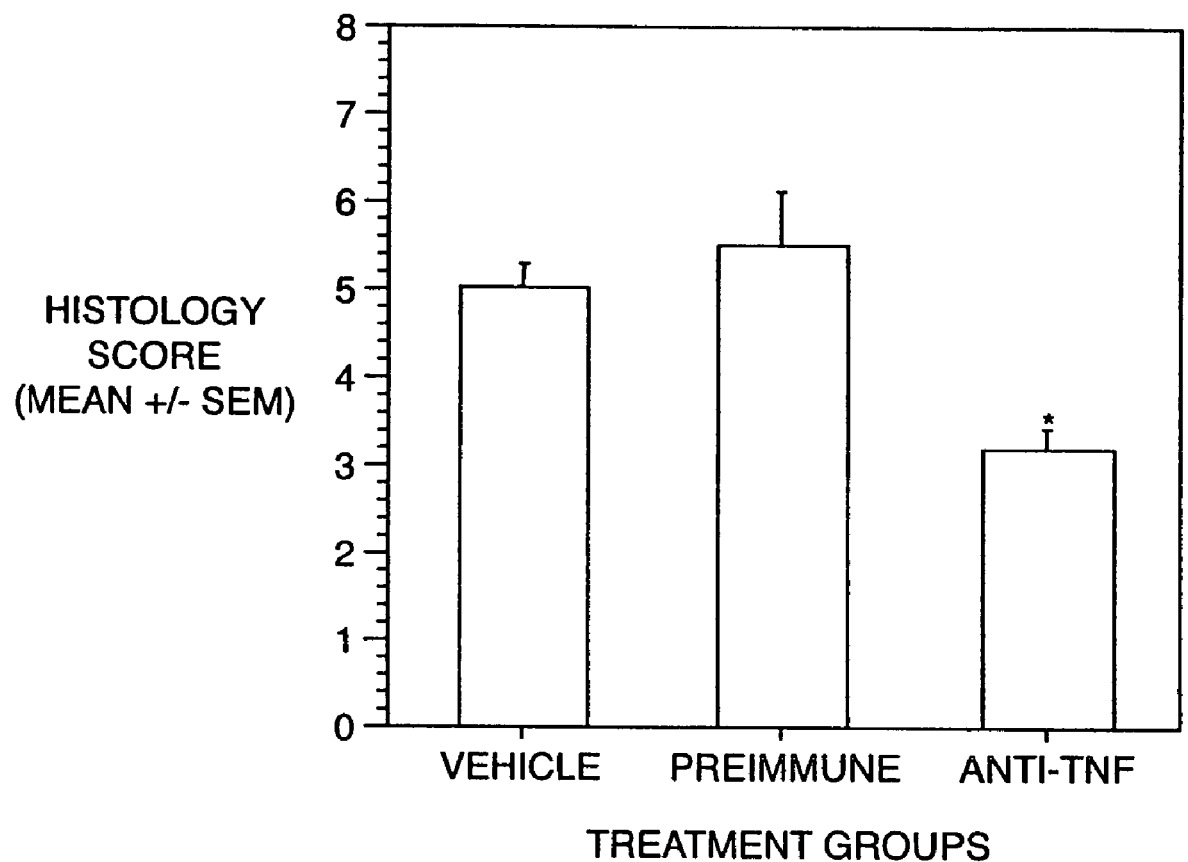
Figure 8C:
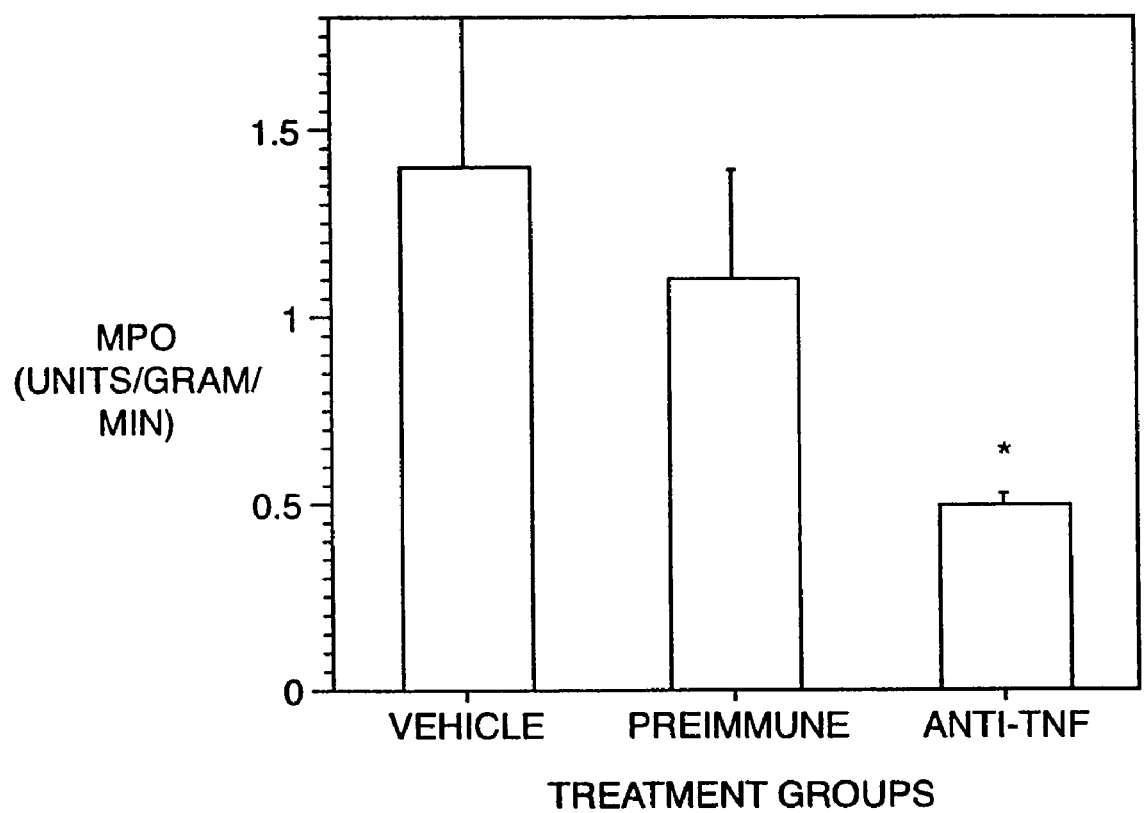

As shown in FIGS. 8A through 8C, treatment with anti-TNF reduces the inflammatory response induced by DSS. The percent positive hemoccult (FIG. 8A), histology.score (FIG. 8.2) and colonic MPO activity (FIG. 8C) were reduced in the anti-TNF treated mice compared to the vehicle or preimmune treated mice.

d) Chronic Treatment Studies

Either CBA/J or C3H/HeJ mice were treated in the chronic stage of the colitis after 3 cycles of DSS. Results of treatment in CBA/J mice after 3 cycles of 5% DSS were collected. The mice were treated with vehicle, preimmune IgY or anti-TNF IgY for 6 days and then tested for fecal blood immediately after treatment and 4 days later. The percentage of hemoccult positive mice 4 days after treatment was reduced in the anti-TNF treated group. The mice were sacrificed, and the histopathology of their colons was assessed. The histology scores were significantly improved in the anti-TNF treated mice.

Results of treatment in C3H/HeJ mice after 3 cycles of 3.5% DSS were collected. After 5 days of treatment with either vehicle, Preimmune, or anti-TNF IgY, the mice were sacrificed, and the histopathology of their colons was assessed. The histology scores were significantly improved in the anti-TNF treated mice.

Example 9

Testing of Anti-IL-6, Anti-IL-8 and Anti-IL-12 (Heterodimer) in a Crohn's Disease Animal Model This example involves the treatment of TNBS-induced colitis during the acute phase of disease with either oral anti-IL-6, anti-IL-8 or anti-IL-12 IgY.

Rats (Sprague Dawley, 200-225 g) were treated acutely with anti-IL-6, anti-IL-8, or anti-IL-12 IgY after TNBS colitis as described above (Example 6, (c), Acute treatment studies). A group of rats were treated with preimmune IgY as a control. Briefly, two days after a rectal TNBS challenge, the rats were treated orally with approximately 100 mg of IgY in two daily doses for five days. The assessment of efficacy for each antibody (colonic weights, colonic morphological evaluation, histology, and biochemical evaluation of MPO activity) was determined exactly as described in Example 6 (a).

The results indicate that, oral anti-IL-6 could effectively treat TNBS-induced colitis compared to preimmune IgY. The effectiveness of anti-IL-6 IgY compared to Preimmune IgY was demonstrated in all four (colon weights, colon damage scores, histology scores, and MPO activity) efficacy parameters. The anti-IL-12 IgY, at the doses tested was partially effective in treating the rats. Specifically, anti-IL-12 IgY gave statistically significant results when evaluating colon weight and gross colonic morphology compared to the preimmune treated rats. In contrast, to both the anti-IL-6 and anti-IL-12, the anti-IL-8 antibody at the doses used and at the current potencies, failed to treat TNBS-colitis with statistical significance compared to the preimmune treated group.

Example 10

Small Bowel Transplantation

The present invention contemplates the use of the anti-cytokine antibodies to inhibit post-transplantation inflammation.

Small bowel transplantation, though still in the early stage of development, is becoming a viable option for persons who suffer intestinal failure as well as very severe cases of Crohn s disease. In the latter case, these patients have a condition known as "short bowel syndrome" because they have lost much of their intestine to surgery. Thus, in order to survive, they must rely on intravenously administered total parenteral nutrition. Although life saving, this treatment is expensive and sometimes can lead to serious infections as well as liver failure.

A Canadian study examined the effectiveness of small bowel transplantation on terminally ill patients who could not be maintained on total parenteral nutrition. A group that had the procedure and had received cylosporine as an immunosuppressive all died. Another group having the same procedure but using FK506 as an immunosuppressive fared better. Obviously, to be an acceptable procedure, small bowel transplantation and the mechanisms leading to its rejection will need to be better understood.

Physicians have speculated that the inflammation profile observed in the small bowel transplant is similar to that of chronic intestinal bowel diseases. It is therefore believed that the mediators of the inflammatory process in small bowel transplant contribute to the deterioration and failure of the intestinal graft. The present invention therefore contemplates that the anti-cytokine antibodies of the present invention (e.g. antibodies to TNF alpha and/or IL-6) will inhibit the inflammatory process.

Such antibodies may be employed pre-transplantation in a preventative mode. On the other hand, such antibodies may be administered post-transplantation as well (e.g. after symptoms arise).

Those skilled in the art will know, or be able to ascertain upon review of the above, using no more than routine experimentation, many equivalents to the specific embodi

What is claimed is:

1. A method comprising:
   a) providing:
      i) a human patient with symptoms of inflammatory bowel disease, and
      ii) a therapeutic formulation comprising antibodies purified from an avian egg yolk, wherein said antibodies are directed to human Tumor Necrosis Factor Alpha; and
   b) administering said formulation to the lumen of the intestine of said patient under conditions such that at least one of said symptoms is reduced.

2. The method of claim 1, wherein said avian egg yolk is a chicken egg yolk.

3. The method of claim 1, wherein said human is a child.

4. The method of claim 1, wherein said administering reduces said symptoms.

5. The method of claim 1, wherein said administering is performed rectally.

6. The method of claim 1, wherein said human has symptoms of ulcerative colitis.

7. The method of claim 1, wherein said human has symptoms of Crohn's disease.

* * * * *